United States Patent
Hunter et al.

(10) Patent No.: US 9,987,037 B2
(45) Date of Patent: Jun. 5, 2018

(54) DEBRIDEMENT APPARATUS USING LINEAR LORENTZ-FORCE MOTORS

(71) Applicant: Massachusetts Institute of Technology, Cambridge, MA (US)

(72) Inventors: Ian W. Hunter, Lincoln, MA (US); Nora Catherine Hogan, Boston, MA (US); Ashley A. Brown, West Chester, PA (US)

(73) Assignee: Massachusetts Institute of Technology, Cambridge, MA (US)

( * ) Notice: Subject to any disclaimer, the term of this patent is extended or adjusted under 35 U.S.C. 154(b) by 216 days.

(21) Appl. No.: 14/705,494

(22) Filed: May 6, 2015

(65) Prior Publication Data

US 2015/0335343 A1 Nov. 26, 2015

Related U.S. Application Data

(60) Provisional application No. 61/989,969, filed on May 7, 2014.

(51) Int. Cl.
*A61B 17/32* (2006.01)
*A61B 17/3203* (2006.01)
(Continued)

(52) U.S. Cl.
CPC .... *A61B 17/3203* (2013.01); *A61B 17/32037* (2013.01); *A61B 17/22* (2013.01);
(Continued)

(58) Field of Classification Search
CPC ...... A61B 17/3203; A61B 2017/00761; A61B 17/32093; A61B 2017/00026;
(Continued)

(56) References Cited

U.S. PATENT DOCUMENTS 4,562,838 A * 1/1986 Walker ............... A61B 18/1402
219/230
4,898,574 A * 2/1990 Uchiyama ........ A61B 17/32037
604/22

(Continued)

FOREIGN PATENT DOCUMENTS

DE 234608 A1 4/1986
WO WO 2003/096871 A2 11/2003
(Continued)

OTHER PUBLICATIONS

Enoch, S. et al., "Wound Bed Preparation: The Science Behind the Removal of Barriers to Healing [Part 1]" *Wounds*, 15(8): 1-27 (Aug. 2003).

(Continued)

*Primary Examiner* — Richard Louis
(74) *Attorney, Agent, or Firm* — Hamilton, Brook, Smith & Reynolds, P.C.

(57) ABSTRACT

A debridement device having a controllable Lorentz-force actuator is disclosed. The debridement device includes a nozzle delivering a jet of debridement substance to a tissue and the jet is driven by the Lorentz-force actuator. The device may have a suction port for removing the debridement substance. A second Lorentz-force actuator can be used for each of the jet and suction. The first and second Lorentz-force actuators for the jet and suction can also be configured to provide for continuous jet injection and continuous suction. The device may include a second nozzle delivering a second jet of debridement substance to the region of tissue and the first and second jets may intersect and dissipate into a mist upon intersection to dissipate the kinetic energy of the jets. The Lorentz-force actuator may drive a reciprocating piston pump providing continuous pressure to the nozzles.

10 Claims, 26 Drawing Sheets

(51) Int. Cl.
*A61B 17/22* (2006.01)
*A61B 17/00* (2006.01)
*A61B 17/3209* (2006.01)
*A61M 1/00* (2006.01)

(52) U.S. Cl.
CPC ............ *A61B 17/32093* (2013.01); *A61B 2017/00026* (2013.01); *A61B 2017/00039* (2013.01); *A61B 2017/00061* (2013.01); *A61B 2017/00084* (2013.01); *A61B 2017/00106* (2013.01); *A61B 2017/00761* (2013.01); *A61B 2017/22079* (2013.01); *A61B 2017/22082* (2013.01); *A61M 1/0084* (2013.01); *A61M 1/0088* (2013.01); *A61M 2205/05* (2013.01)

(58) Field of Classification Search
CPC ........... A61B 2017/00106; A61B 2017/00061; A61B 2017/00084; A61B 2017/22082; A61B 2017/22079; A61B 17/22; A61B 2017/00039; A61B 2017/32035; A61B 17/32037; A61M 1/008; A61M 2205/05; A61M 1/0088; A61M 1/0084
See application file for complete search history.

(56) References Cited

U.S. PATENT DOCUMENTS

| | | | | |
|---|---|---|---|---|
| 5,037,431 | A * | 8/1991 | Summers | A61B 17/3203 604/22 |
| 6,241,710 | B1 * | 6/2001 | VanTassel | A61M 5/3286 604/264 |
| 6,451,017 | B1 | 9/2002 | Moutafis et al. | |
| 7,833,189 | B2 | 11/2010 | Hunter et al. | |
| 8,172,790 | B2 | 5/2012 | Hunter et al. | |
| 2001/0029365 | A1 * | 10/2001 | Nagahori | B23K 26/1494 606/13 |
| 2003/0100835 | A1 * | 5/2003 | Da Silva | A61B 5/0084 600/476 |
| 2003/0125660 | A1 | 7/2003 | Moutafis et al. | |
| 2003/0175410 | A1 * | 9/2003 | Campbell | A61L 27/38 427/2.24 |
| 2004/0092925 | A1 * | 5/2004 | Rizoiu | B23K 26/146 606/33 |
| 2004/0127925 | A1 * | 7/2004 | Du | A61B 17/22012 606/167 |
| 2006/0258986 | A1 * | 11/2006 | Hunter | A61D 7/00 604/164.01 |
| 2007/0129630 | A1 | 6/2007 | Shimko | |
| 2008/0009788 | A1 | 1/2008 | Hunter et al. | |
| 2008/0177258 | A1 * | 7/2008 | Govari | A61B 18/1492 606/41 |
| 2009/0069805 | A1 | 3/2009 | Fischer et al. | |
| 2009/0254075 | A1 | 10/2009 | Paz et al. | |
| 2009/0312696 | A1 * | 12/2009 | Copa | A61M 25/007 604/43 |
| 2009/0326489 | A1 | 12/2009 | Kensy et al. | |
| 2011/0015627 | A1 * | 1/2011 | DiNardo | A61B 17/320092 606/34 |
| 2011/0082388 | A1 | 4/2011 | Hunter et al. | |
| 2011/0143310 | A1 | 6/2011 | Hunter | |
| 2011/0245757 | A1 | 10/2011 | Myntti et al. | |
| 2011/0264057 | A1 * | 10/2011 | Eversull | A61L 29/085 604/265 |
| 2011/0311939 | A1 | 12/2011 | Hunter et al. | |

FOREIGN PATENT DOCUMENTS

| | | |
|---|---|---|
| WO | WO 2004/037095 A2 | 5/2004 |
| WO | WO 2006/08677 A2 | 8/2006 |
| WO | WO 2006/086719 | 8/2006 |
| WO | WO2008/027579 A1 | 3/2008 |
| WO | WO 2010/148125 A1 | 12/2010 |
| WO | WO2011/075535 | 6/2011 |
| WO | WO 2011/075545 A1 | 6/2011 |
| WO | WO 2012/068735 A1 | 5/2012 |
| WO | WO 2014/210149 A1 | 12/2014 |
| WO | WO2015/171754 | 11/2015 |

OTHER PUBLICATIONS

Granick, M. S., et al., "Efficacy and cost-effectiveness of a high-powered parallel waterjet for wound debridement", *Wound Repair and Regeneration*, 14: 394-397 (2006).

Guo, S. and DiPietro, L.A., "Factors affecting wound healing", *J. Dental Res.*, 89(3): 219-229 (2010).

Gupta, S., "Differentiating Negative Pressure Wound Therapy Devices: An Illustrative Case Series", *Supplement to Wounds*, 19(1): 1-10 (Jan. 2007).

Hassinger, S. M. et al., "High-pressure pulsatile lavage propagates bacteria into soft tissue", *Clinical Orthopaedics and Related Research*, 439: 27-31 (Oct. 2005).

Hogan, N. C. et al., Delivery of Active Collagenase to Skin Using a Lorentz-Force Actuated Needle-Free Injector, Conference Proceedings IEEE Eng. Med. Biol., Soc., 1: 5611-5616 (Aug. 30-Sep. 3, 2006).

Jones, S. M. et al., "Advances in wound healing: topical negative pressure therapy", *Postgrad Medical Journal*, 81: 353-357 (2005).

Klein, M. G. et al., "The Versajet™ Water Dissector: A New Tool for Tangential Excision", *Journal of Burn Care & Rehabilitation*, 26: 483-487 (Nov./Dec. 2005).

McAleer, J. P. et al., "A Prospective Randomized Study Evaluating the Time Efficiency of the VERSAJET Hydrosurgery System and Traditional Wound Debridement", Wound Management, Smith & Nephew (2006).

Mercandetti, M., "Wound Healing and Repair", MEDSCAPE Reference. Retrieved from Internet URL: http://emedicine.medscape.com/article/1298129-overview. Retrieved from Internet on Aug. 12, 2015.

Moore, Z., "Technology Update: The important role of debridement in wound bed preparation", *Wounds International*, 3(2): 19-23, (2012).

Occupational Safety and Health Guide for Acetic Acid. Retrieved from Internet URL:http://pmj.bmp.com/Jones.

Rau, H. G. et al., "The use of water-jet dissection in open an laparoscopic liver resection", *HPB*, 10: 275-280 (2008).

Saxena, S. M. et al., "Vacuum-Assisted Closure: Microdeformations of Wounds and Cell Proliferation", *Plastic and Reconstructive Surgery*, 114(5): 1086-1096 (Oct. 2004).

Schultz, G. S. et al., "Wound bed preparation: a systematic approach to wound management", *Wound Repair and Regeneration*, 11(2): S1-S28 (Mar.-Apr. 2003).

Smith & Nephew VERSAJET II Hydrosurgery System, User Guide. Smith & Nephew, Inc.

Sullivan, N. et al., "Technology Assessment: Negative Pressure Wound Therapy Devices", Prepared for: Agency for Healthcare Research and Quality (May 26, 2009).

Taberner, A. et al., "Needle-free jet injection using real-time controlled linear Lorentz-force actuators", *Medical Engineering & Physics*, 34: 1228-1235 (2012).

Taberner, A. J. et al., A Portable Needle-free Jet Injector Based on a Custom High Power-density Voice-coil Actuator, Conference Proceedings IEEE Eng. Med. Biol. Soc., 1: 5001-5004 (Aug. 30-Sep. 3, 2006).

Witte, M. B. and Barbul, A., "General Principles of Wound Healing", *Surgical Clinics of North America*, 77(3): 509-528 (Jun. 1997).

Bradley, M., et al., "The Debridement of Chronic Wounds: A Systematic Review", *Health Technology Assessment*, vol. 3: No. 17 (Pt. 1) (1999).

Oertel, J., et al., "Waterjet Dissection in the Brain: Review of the Experimental and Clinical Data with Special Reference to Meningioma Surgery", *Neurosurg Rev* (2003) 26:168-174.

The International Search Report and Written Opinion of the International Searching Authority dated Sep. 30, 2015 for International

(56) References Cited

OTHER PUBLICATIONS

Application No. PCT/US2015/029456, entitled "Debridement Apparatus Using Linear Lorentz-Force Motors".

Notification Concerning Transmittal of International Preliminary Report on Patentability and International Preliminary Report on Patentability, "Debridement Apparatus Using Linear Lorentz-Force Motors," PCT/US2015/029456, dated Nov. 17, 2016.

* cited by examiner

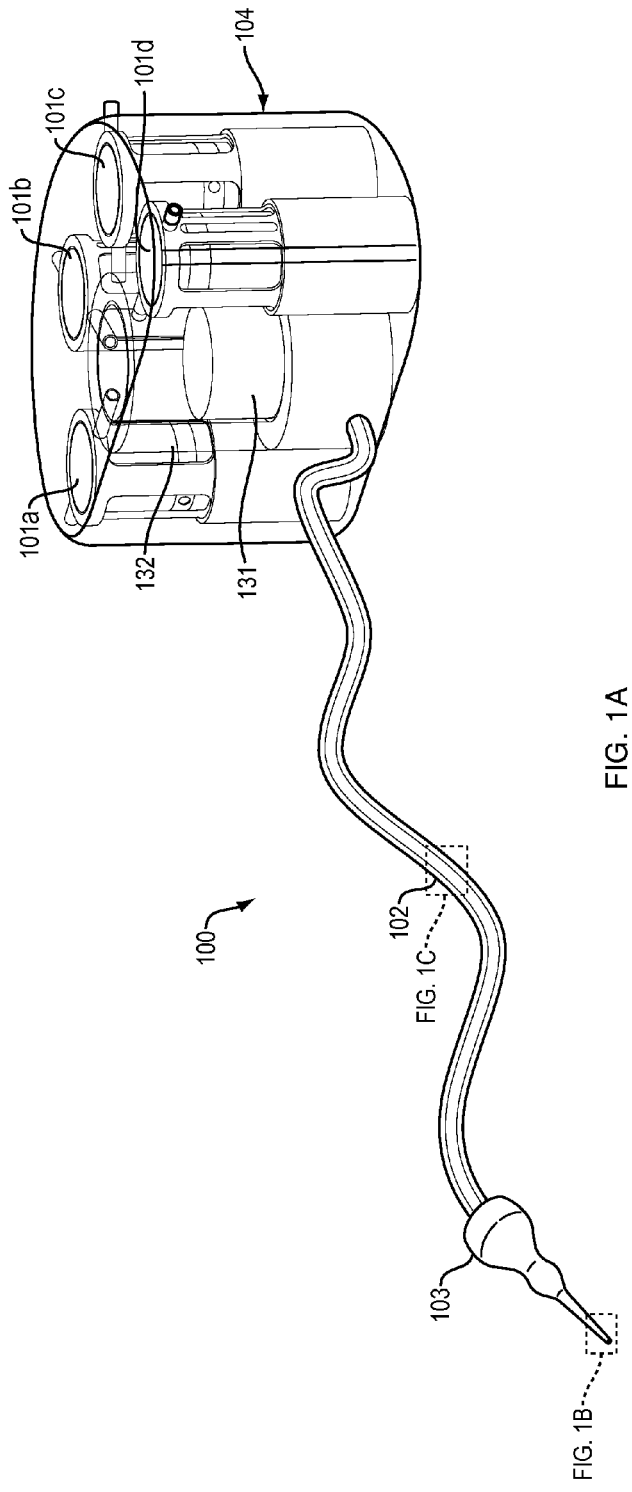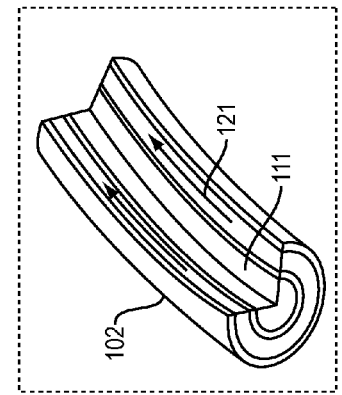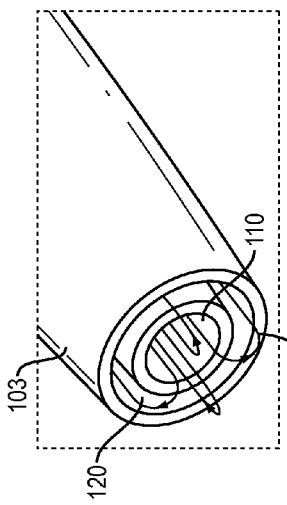
FIG. 1A
FIG. 1B
FIG. 1C

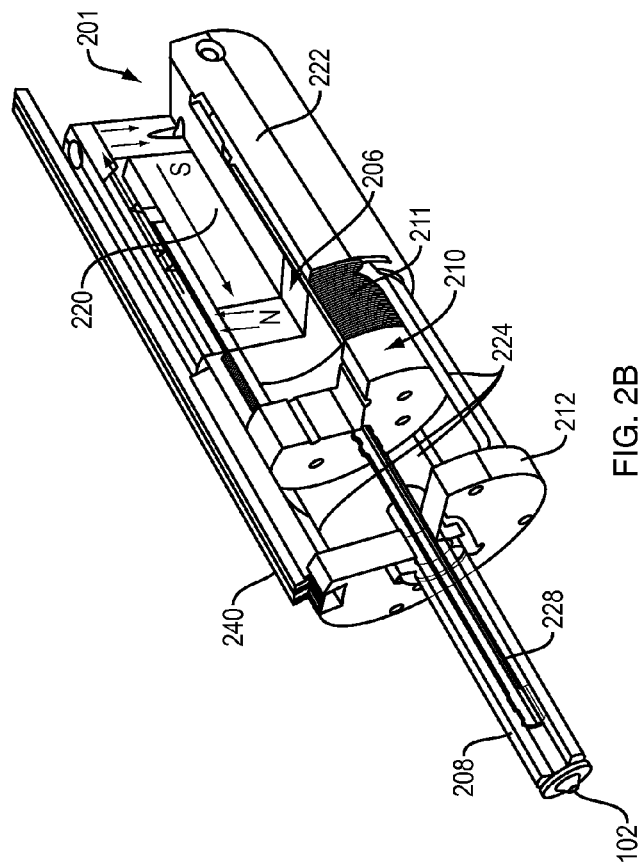
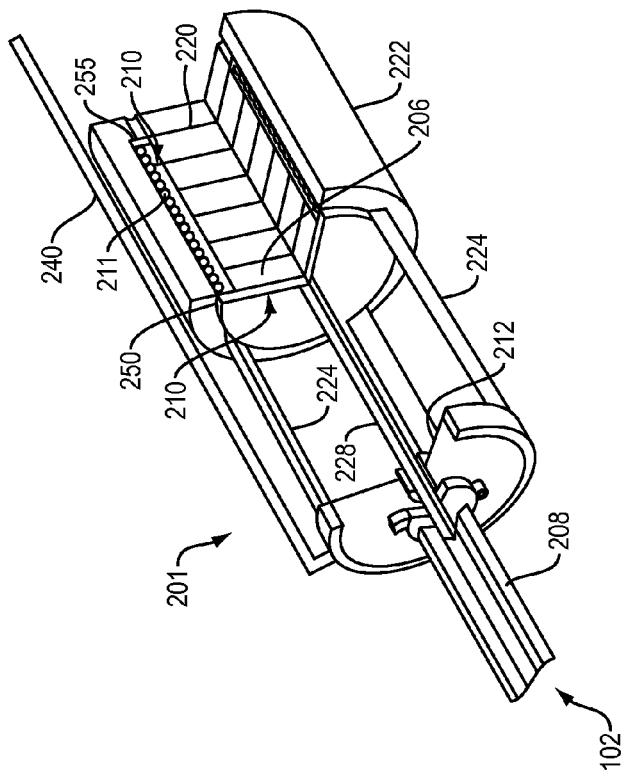
FIG. 2B
FIG. 2A

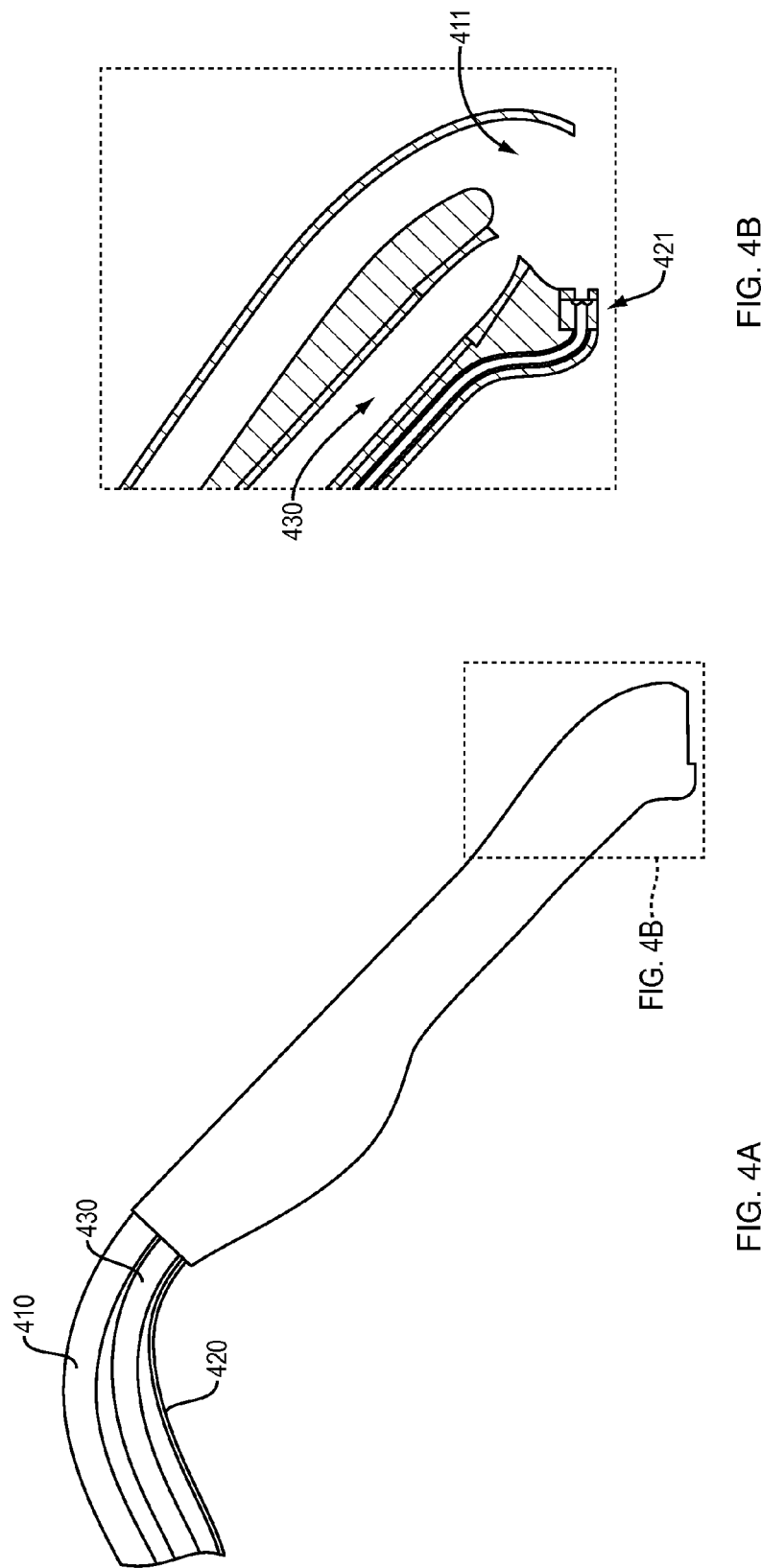

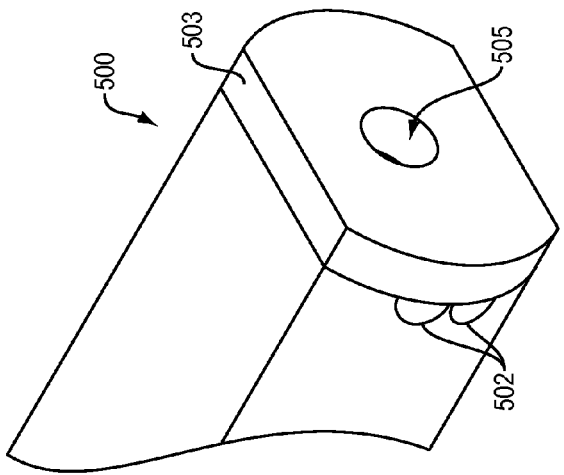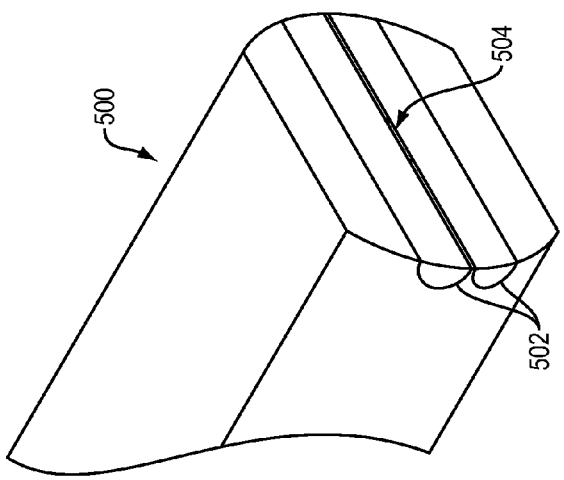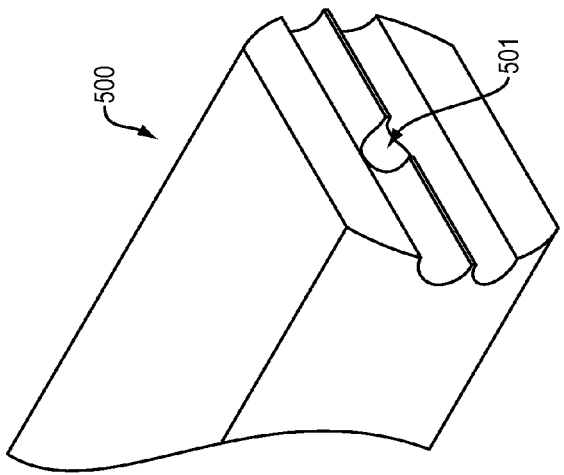

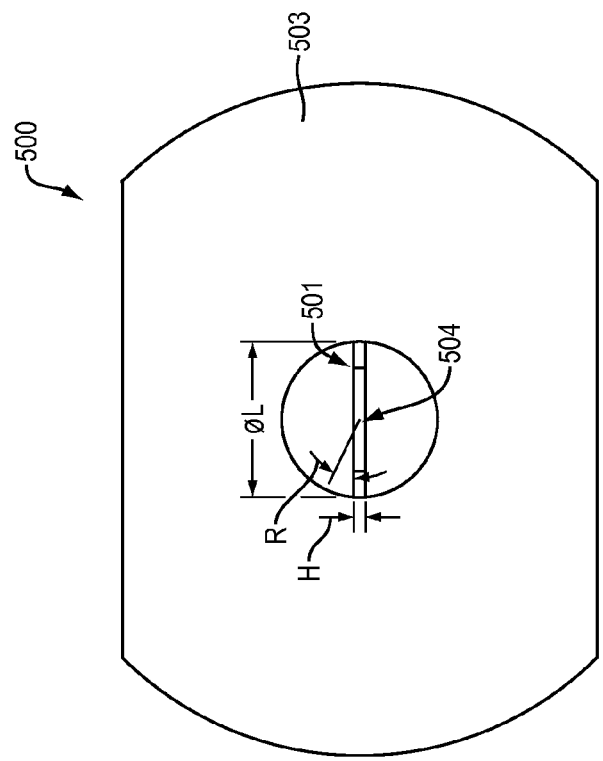
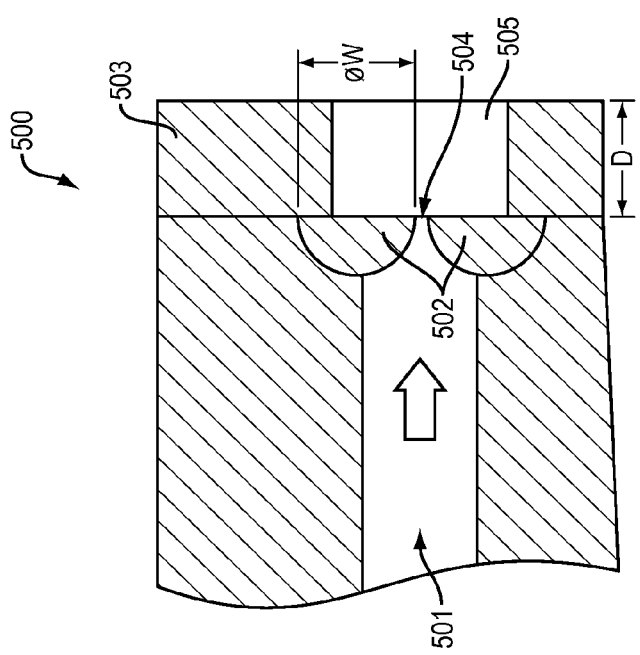

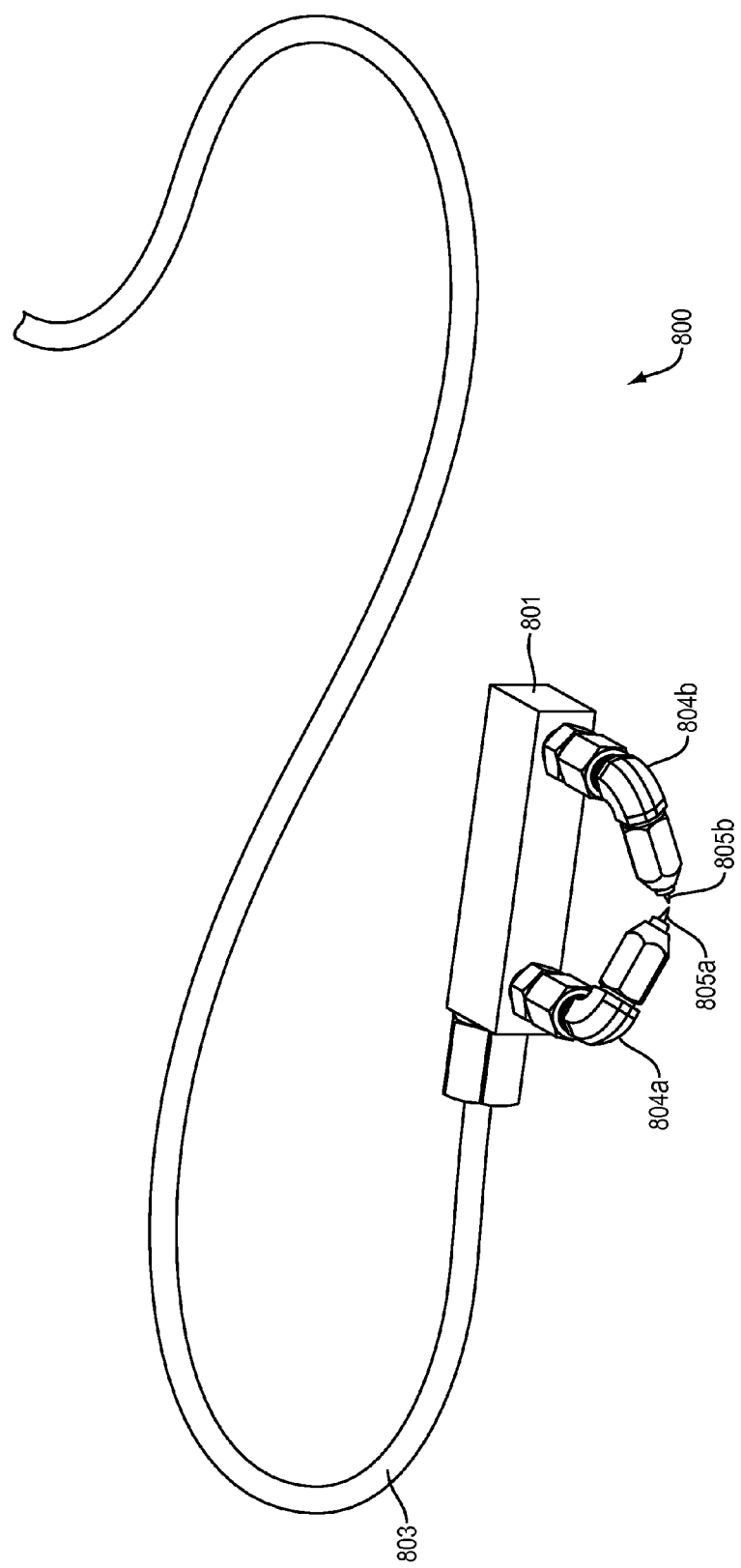

REMOVAL OF EXCISED TISSUE

EXCISION OF NECROTIC TISSUE

120° INTERSECTION, TIPS
4 mm APART NO TISSUE

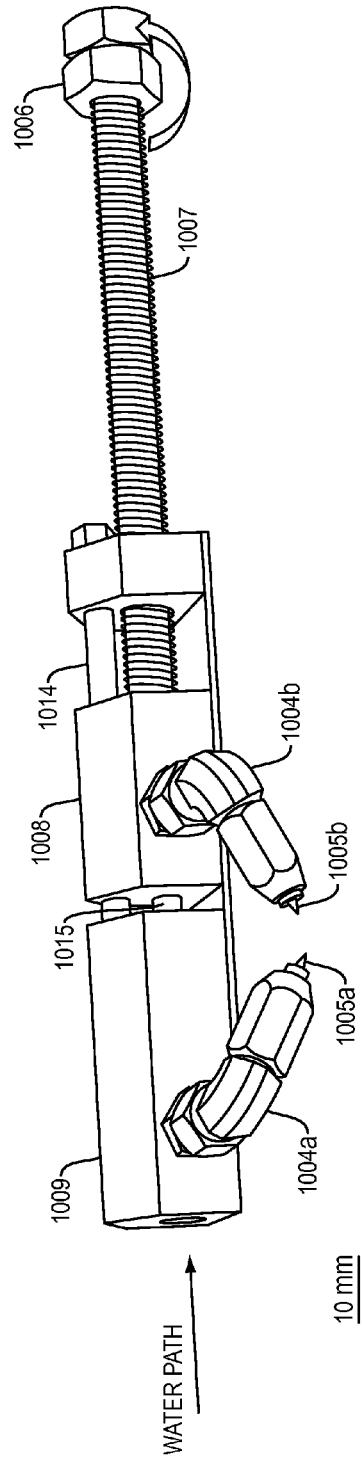
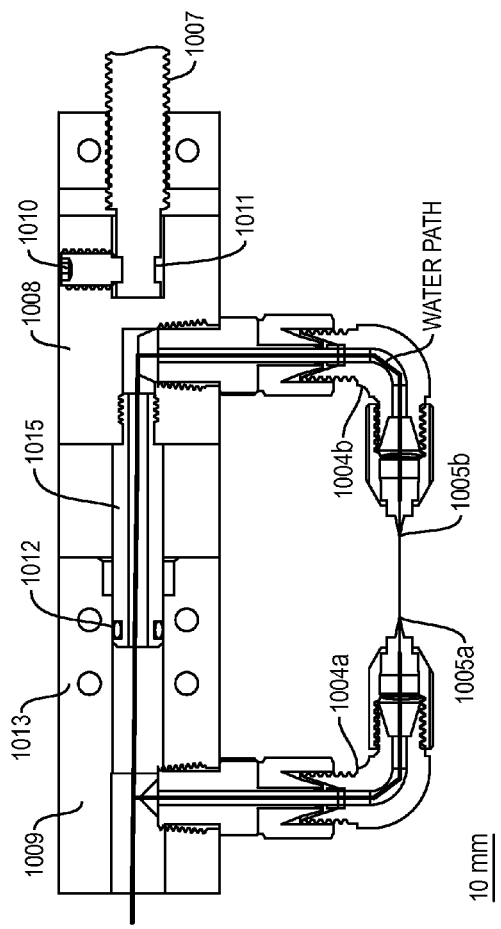

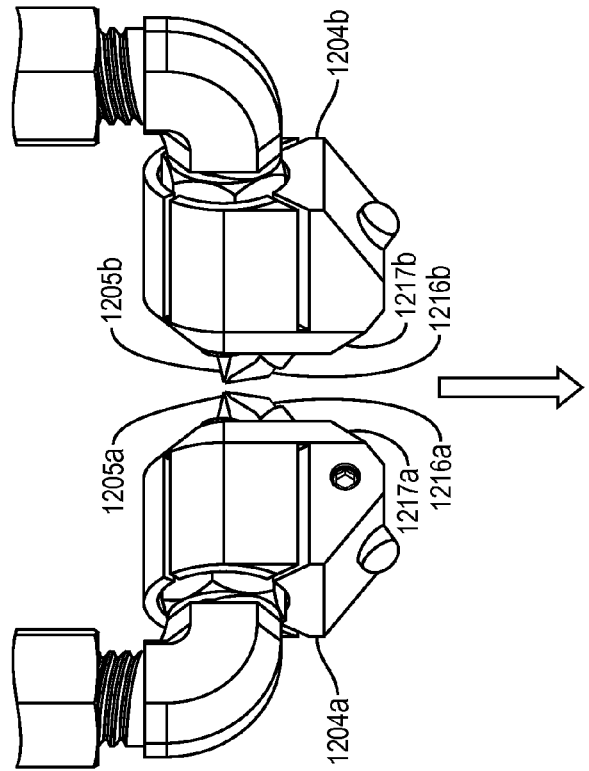
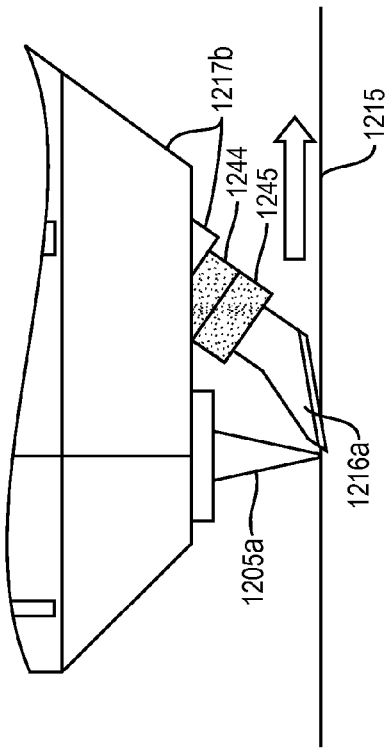
FIG. 12B
FIG. 12A

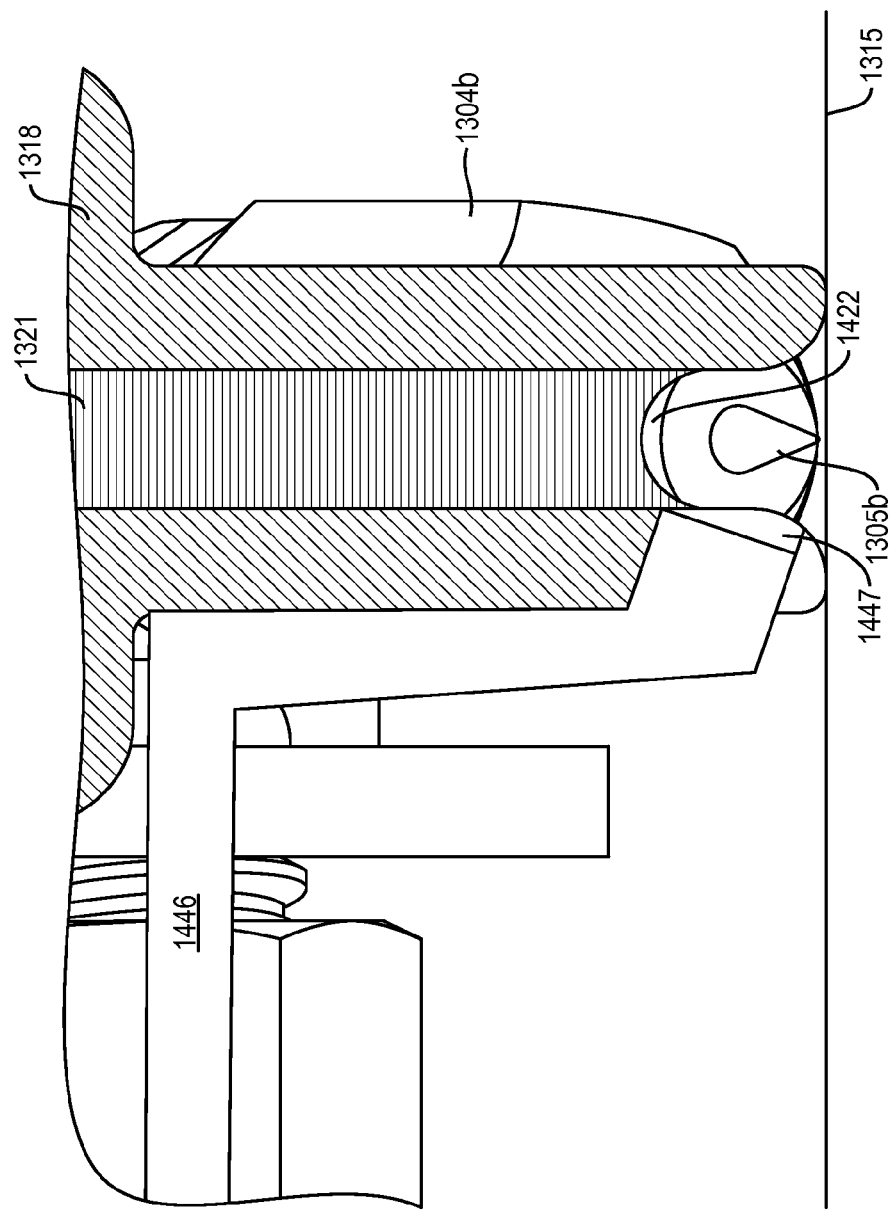

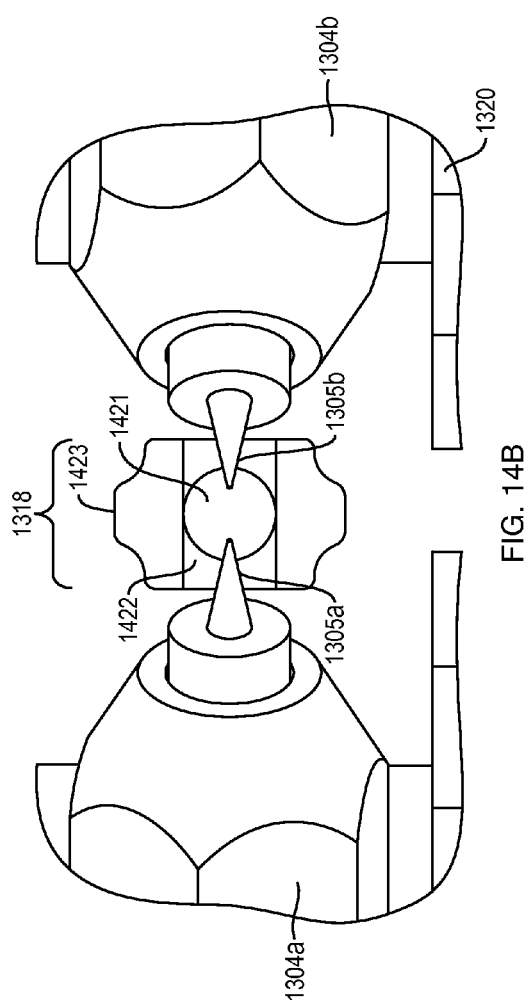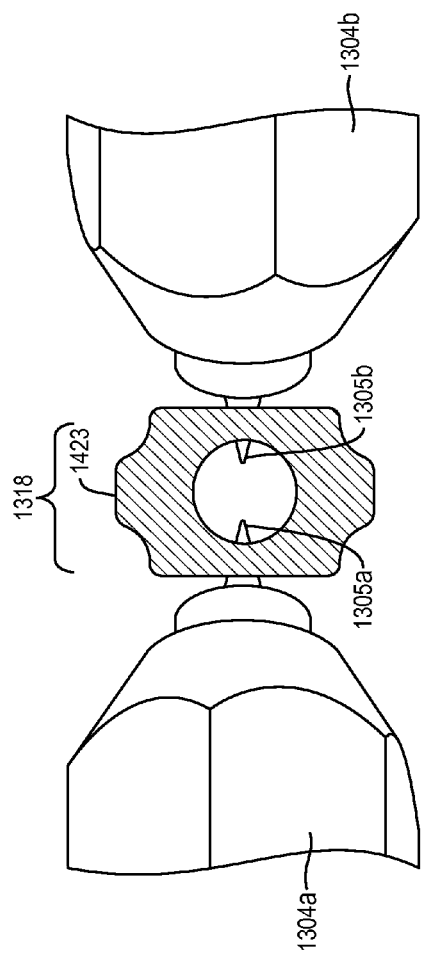
FIG. 14B
FIG. 14C

DEBRIDEMENT APPARATUS USING LINEAR LORENTZ-FORCE MOTORS

RELATED APPLICATION(S)

This application claims the benefit of U.S. Provisional Application No. 61/989,969, filed on May 7, 2014. The entire teachings of the above application are incorporated herein by reference.

BACKGROUND

Wound healing generally progresses through four stages: coagulation, inflammation, cell proliferation and repair of the extracellular matrix (ECM), and finally epithelialization and remodeling to form scar tissue (for reviews, see [1][2][3]). Chronic wound healing, while initially thought to represent an aberration of the normal tissue repair process, is now recognized as being different from normal wound healing. In chronic wounds, remodeling of the ECM is defective, re-epithelialization fails, and the tissue remains inflamed; the wound repair process becomes "stuck" in the inflammatory and/or proliferative stage. Resumption of the process requires identification and removal of the barriers to healing, broadly referred to as wound bed management.

Debridement and subsequent negative pressure wound therapy (NPWT) are crucial components in wound management (for reviews, see [5][6][7]). Current methods of debridement include surgical, mechanical, autolytic, enzymatic, or larval (see [8]). Cost, skills/training, and patient acceptance need to be considered when choosing which method will be most effective. Surgical debridement does not adequately define the border between non-viable and viable tissue and is costly while chemical methods of debridement are slow and require multiple treatments, which requires patient compliance [9].

SUMMARY OF THE INVENTION

Example embodiments include a debridement apparatus comprising a controllable Lorentz-force electromagnetic actuator system having at least one coil and at least one magnet assembly, a nozzle delivering a jet of debridement substance to a region of tissue, the jet being driven by the controllable Lorentz-force electromagnetic actuator, and a suction port for removing the debridement substance after delivery to the region of tissue and additional substances therein, the suction port supporting a negative pressure for suction, and the negative pressure supplied by the controllable Lorentz-force electromagnetic actuator. The pressures of the jet and suction can define pressure profiles for at least one of the following: cutting tissue, stimulating tissue for regeneration, breaking up material for removal, stimulating healthy tissue to assist healing. The pressure profiles can correspond to a predetermined or sensed frequency resonance of the tissue region. The nozzle and suction port can be configured in a coaxial nozzle, the coaxial nozzle defining an inner nozzle and an outer suction port.

In some embodiments, the Lorentz-force actuator is adapted to drive the jet with pulses of the debridement substance. The debridement apparatus can include a first Lorentz-force actuator for each of the jet and suction. A second Lorentz-force actuator can be used for each of the jet and suction. The first and second Lorentz-force actuators of the jet and suction can be configured to provide for continuous jet injection and continuous suction.

The apparatus can include a reservoir of debridement substance and a waste reservoir adapted to receive substances retrieved through the suction port. The apparatus can also include a sensor determining properties of the debridement substance for controlling the actuator.

Another example embodiment is a debridement apparatus comprising a first nozzle delivering a first jet of debridement substance to a region of tissue at a first angle, a second nozzle positioned a distance away from the first nozzle, the second nozzle delivering a second jet of debridement substance to the region of tissue at a second angle, the second jet driven by the controllable pressure source. Wherein the first and second jets are adapted to intersect and dissipate into a mist upon intersection, wherein the mist dissipates substantially the kinetic energy of the first and second jet. At least one of the first angle, the second angle, and the distance can be adjustable. The apparatus can include a controllable pressure source driving the first and second jet. The controllable pressure source can include at least one Lorentz-force electromagnetic actuator.

In some embodiments, the apparatus includes an evacuation chamber supporting a negative pressure and positioned between the first and second nozzles. The evacuation chamber can include a distal end configured to interface with the region of target tissue and stabilize the region of tissue while removing debrided tissue, contaminants, and exudate through an evacuation lumen coupled to the evacuation chamber. The evacuation chamber can include a cavity or slot to receive the first and second nozzles.

An embodiment of the present invention is a debridement apparatus with Lorentz-force motors, the debridement apparatus comprising a controllable Lorentz force electromagnetic actuator comprising at least one moving coil and at least one stationary magnet assembly, a nozzle delivering a jet of debridement substance to a region of tissue, said jet driven by the controllable Lorentz force electromagnetic actuator, and a suction port for removing the debridement substance and additional substances therein, the suction port supporting a negative pressure.

An embodiment is a debridement device incorporating the Lorentz-force motors, the device uses two sets of dual actuators, each of which operates in reciprocation. One set is in fluid communication with the inner most reservoir, for example, a drug-filled reservoir, of central concentric reservoirs and delivers a specified volume of fluid, e.g., a drug, at a pre-defined velocity and time interval to the tissue in a reciprocating manner. The second set of actuators can be in communication with the outermost concentric reservoir and can remove or "suck" exudate and necrotic, damaged, or infected tissue from the wound bed via a second pre-defined waveform. This set up can ensure that fluid delivery for debridement and removal of irrigant and wound contents can be performed without interruption. Dual Lorentz-force actuators are, for example, described in U.S. Pat. No. 8,398,583, the teachings of which are incorporated by reference in their entirety.

In other embodiments, the nozzle, through which liquid at variable jet velocities may be delivered to the target, has a diameter ranging from 50 to 200 µm. The nozzle may contain internal surface geometry that affects jet flow. In an example embodiment, the internal surface of the inner nozzle includes a smoothly tapered shape to provide a more collimated flow desired for precise cutting.

When operated at low fluid pressures (i.e. low velocities), an example embodiment is used for lavage and/or debridement without substantial cutting as might be the case when removing exudate. Removal of exudate is accomplished by reversing the direction of one or more of the actuators, e.g., the set of actuators communicating with the outer concentric ring forming the distal tip. In another embodiment, the shape of the outer concentric ring forming the distal tip may vary from circular through to elliptical and have variable inner diameters relative to the nozzle. In yet another embodiment, an elliptical shape reduces or prevents blockage that could result from evacuation of larger pieces of tissue.

Embodiments can use liquid, slurry, or even a powder as a debridement fluid. One embodiment uses four Lorentz-force motors, two for continuous suction, and two for continuous jet injection. Fewer motors can be used. For example, one motor can be used for both injection and suction in a dual-purpose configuration with a valve to facilitate driving the jet and suction.

Lorentz-force actuators or motors are able to operate close to the speed of sound. The actuators or motors are able to provide jet velocities of at least 200 m/s, or up to or above 500 m/s, and pressure up to 100 MPa while providing an extremely high level of pressure control. Lorentz—force actuators have advantages, including being able to stop faster than prior art (e.g. rotary pumps) devices because the Lorentz-force actuators are driven in—a reciprocating manner with no rotational inertia to overcome. They are also able to generate a constant force throughout their linear travel, in contrast to solenoid-type devices. In addition, when used in tandem for continuous suction or injection, Lorentz-force actuators are able to create opposing forces to retard their motion faster than could be done individually.

Other embodiments pulse the Lorentz-force motors to deliver a pulse of fluid instead of a continuous stream. Example embodiments of the pulsing configuration have a pulse cycle time (pressure vs. time) optimized for certain tissues and debridement conditions, for example, having a 10 ms jet followed by a 10 ms refill period for a 20 ms actuator cycle time. Embodiments can achieve a higher energy range by using a piezoelectric actuator in the fluid flow. Piezoelectric devices have been combined with Lorentz-force actuators before, as in dental cleaning applications described in US 20110143310 A1, incorporated herein by reference, which describes adding low power oscillations to a fluid jet to measure tissue properties. Higher power piezoelectric slabs can be used to increase the frequency bandwidth of the jet and to increase power.

Some examples include or employ a sensor to determine healthy tissue from damaged tissue. Such sensors can make use of mechanical or electrical impedance measurements or use the fluid jet or a perturbation to the jet to measure mechanical properties of the tissue in contact with the fluid and servo-control the jets based on this feedback. Likewise, acoustic sensors can use the injection fluid as a medium to perform diagnostic measurements. Acoustic, near IR, surface enhanced Raman scattering (SERS) and optical fibers can also be used to evaluate the wound bed and surrounding tissue.

Embodiments may have multiple modes for jet and suction. Such modes include cutting, stimulating tissue for regeneration, and breaking up material for removal. Other embodiments have pressure profiles for stimulating healthy tissue to assist healing. Still other embodiments have pressure profiles corresponding to a predetermined or sensed frequency resonance of the tissue being treated, e.g., to assist in the debridement.

Embodiments of the present invention have nozzles designed to avoid splatter or cross-contamination between regions outside of the immediate location of the jet flow. In one embodiment, this is accomplished by positioning the nozzle tips within a cavity or slot created in the end of the evacuation chamber which serves to shield the area around the nozzles.

Embodiments of the present invention have various nozzle geometries to tailor the profile of the jet of debridement fluid. Embodiments may have positive geometry rifling in the nozzle to induce rotational energy to the fluid flow.

Some embodiments of the present invention have a concentric nozzle with a jet flow surrounded by a suction flow. Other embodiments have different suction locations to optimize the intake of fluids associated with the debridement from the jet nozzle.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale; emphasis instead being placed upon illustrating embodiments of the present invention.

FIGS. 1A-E are illustrations of an example device that can be used for debridement according to an embodiment of the present invention.

FIGS. 2A-B are cut-away views of example linear Lorentz-force actuated jet injectors used in the present invention.

FIGS. 4A-B are views of an example embodiment of the present invention showing the hand piece of the device and an additional tube that delivers fluid under low pressure to control the distance over which the fluid exiting the nozzles cuts.

FIGS. 5A-C are isometric views of a nozzle assembly.

FIGS. 7A-B are sectional and front views, respectively, of a completed nozzle assembly.

FIG. 8 is a view of another embodiment of the present invention showing a hand piece with a first and second nozzle orifice.

FIGS. 10A-B are perspective and section views, respectively, of an example hand piece with first and second nozzles.

FIGS. 12A-B illustrate an example embodiment of a debridement device that includes a surgical blade mounted adjacent to each nozzle to score the tissue prior to tissue cutting and removal using the liquid jets.

FIGS. 14A-C show enlarged views of the vacuum channel and the relative position of the nozzle arms, and nozzle jets with respect to the vacuum chamber of the device illustrated in FIG. 13A.

DESCRIPTION OF EXAMPLE EMBODIMENTS THE INVENTION

Figure 1E:
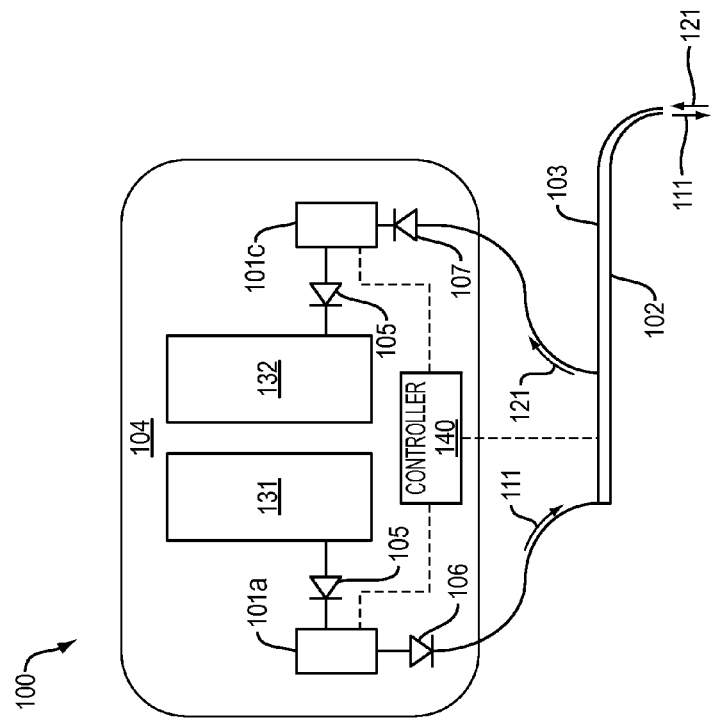

A description of example embodiments of the invention follows.

Waterjet dissection has been used for several decades in for example liver, kidney, brain, and laparoscopic surgery (see [10][11]). More recently, high-pressure waterjets have found use in wound debridement (see [12][13]), as have ultrasonic devices (e.g. MIST®, Misonix SonicOne®, Arobella Qoustic™, etc. see [14]). Highly collimated liquid jets are preferred for cutting tissue. With the VERSAJET™ device (US2010/0094313 A1), a high pressure pump is used to generate a narrow stream of fluid that is expelled from a nozzle, the design of which provides an enhanced vena contracta effect (US2006/0264808 A1; U.S. Pat. No. 6,375,635 B1); the resultant jet stream remains collimated over a greater jet length than typical. The construction and position of the pressure lumen and evacuation lumen relative to each other ensure that the liquid jet and any tissue or material entrained by the jet can be evacuated without the need for an external source of suction (U.S. Pat. No. 6,375,635 B1). Debridement is accomplished in a single step utilizing a relatively small amount of irrigant thereby minimizing saturation of the target tissue and reducing the risk of splashing and aerosolization. The nozzle diameter, position of the center of the fluid opening, and deck height (i.e. the distance between the center of the fluid opening and the deck or opening in the jet channel interacting with the air and tissue) affect precision (US2010/0094313 A1; US2006/0264808 A1).

The VERSAJET™ device variably controls the velocity of the liquid jet using a high-pressure pump assembly; depressing a foot pedal activates the cutting jet, depressing a toe button increases or decreases the power setting dependent on UP or DOWN arrows (see [15]). Current waterjet technologies use pumps requiring user operator control, which is often accomplished via foot pedals.

Present embodiments relate to a novel jet technology using an electrically driven linear Lorentz force motor to generate the precisely controlled pressures (velocities) for debridement. At the heart of the technology is a magnet surrounded by a coil of wire. Current delivered to the coil generates a Lorentz-force which drives the piston and by extension the fluid through a nozzle. Using a linear Lorentz-force motor permits precise control over the depth and velocity of the liquid jet via high-speed monitoring and servo control of the voice coil motor. Inclusion of sensors provides electrical feedback permitting the velocity to be altered based on tissue properties. The feedback can be used to servo control the actuator driving the jet. The depth of delivery has been shown to be dependent on the initial velocity ($V_{jet}$) and the time spent at $V_{jet}$ ($T_{jet}$) (see [16][17]). Further, this device can both deliver and extract fluid; it is bi-directional (U.S. Pat. No. 7,833,189 B2; U.S. Pat. No. 8,328,755 B2; US2011/0082388 A1).

In the context of wound management, the present invention permits the wound bed to be cleansed using low-pressure lavage followed by brief high-pressure pulses to remove dead, damaged, or infected tissue. This can then be followed by continual or intermittent low-pressure lavage under suction. This type of scenario can prevent the penetration, retention, and propagation of bacteria as discussed in [18] while at the same time promoting cleaning and drainage of the wound bed by intermittent irrigation and suction. Delivery and removal of fluid across the wound bed under vacuum causes micromechanical forces, in addition to those produced by suction alone, to be transmitted to the tissue causing further deformations of the local ECM and may improve cellular proliferation, release of growth factors, and angiogenesis [19][20], which are involved in the formation of granulation tissue.

Chronic wounds are characterized by devitalized tissue and excess exudate that either form a hard eschar or slough [5]. Removal of necrotic tissue and re-establishing bacterial and fluid imbalance are requisite to wound healing. Evaluation of instrumentation for debridement can include mimicking some of the properties of a wound bed. Slough can be generated by treating post mortem tissue with acetic acid having a concentration ranging from 50 to 60%[21]. Enzymes such as bacterial collagenase [22] or trypsin (both used for enzymatic debridement [23]) may also be used to partially digest areas of tissue (e.g. muscle) and removal of damaged tissue evaluated as described. The jet pressure (jet velocity or $V_{jet}$) along with the $T_{jet}$ required to separate the necrotic tissue from the surrounding undamaged tissue can be evaluated empirically while inclusion of fluorescently labeled bacteria, colored beads, or tissue marking dyes can provide a measure of the ability to controllably switch between a high velocity jet and a much lower velocity lavage for both precise removal of damaged tissue and assessment of bacterial load and damage to residual tissue. Assuming a fixed inner diameter for the nozzle (50 to 200 μm), there exists a range of outer nozzle diameters, for example, 2 to 20 millimeters that may be employed to remove debris from the wound bed. In addition, the timing and velocity required for removal can be changed based on debridement requirements.

The device may house one or more sensors that can detect respective physical properties of the tissue, said properties being used to servo-control the actuator permitting tailoring of the pressure vs. time profile throughout the course of the debridement. For example, mechanical impedance, near IR, SERS, optical and acoustic sensors could be used to differentiate healthy tissue from tissue requiring debridement. In addition, mechanical or electrical impedance sensors could be used to assess scoring of the tissue while force sensors and gyrometers could be used to assess tissue load and device orientation respectively. Additional considerations are given to prevention of exposure to blood borne pathogens either in solid or aerosolized form during treatment.

Lorentz-force motors that can be used in embodiments, for example, for driving the delivery of fluid and its evacuation along with exudate and tissue debris are described in U.S. Pat. No. 7,833,189 B2, U.S. Pat. No. 8,328,755 B2, U.S. Pat. No. 8,172,790 B2, and [16], and are incorporated by reference in their entirety.

The embodiment shown in FIG. 1A is a debridement apparatus 100 with Lorentz-force actuators 101a-d. The debridement apparatus 100 comprises controllable Lorentz force electromagnetic actuators 101a-d each including at least one moving coil and at least one stationary magnet assembly, tubing 102 delivering a debridement substance from the actuators 101a-d to a nozzle assembly 103, two central concentric reservoirs one reservoir 131 delivering a specified volume of debridement substance at a predefined velocity and time interval to the tissue through a nozzle 110 and a second reservoir 132 into which waste material from the wound bed is collected during debridement. FIG. 1B shows the nozzle 110 delivering a jet of debridement substance 111, for example, a fluid, drug, or slurry, (shown as arrows 111 leaving the nozzle 110) to a region of tissue (not shown) and a suction port 120 for removing the debridement substance and additional substances therein 121, the suction port supporting a negative pressure. The nozzle 110 can include internal geometry or a collimator to condition the flow of debridement substance before exiting the nozzle 110. FIG. 1C shows a cut away view of the coaxial structure of the tubing 102. The tubing 102 comprises an inner tube, the lumen of which serves to supply the debridement substance 111 or irrigant to the nozzle assembly (103 in FIG. 1A) and an outer lumen or suction port that transfers irrigant and material such as exudate, necrotic or damaged tissue 121 collected from the wound bed via the nozzle assembly (103 in FIG. 1A) to a reservoir 132 in the apparatus housing (104 FIG. 1A).

Figure 1D:
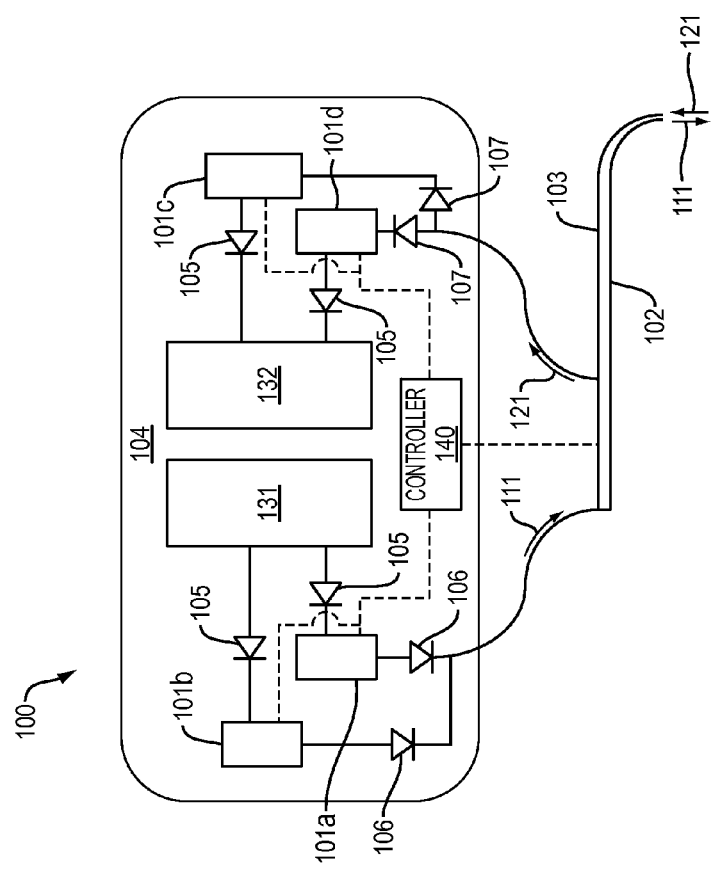

FIG. 1D shows a diagram of the debridement apparatus illustrated in FIG. 1A incorporating four Lorentz-force actuators 101a-d. The device 100 uses two sets of dual actuators, each of which operates in reciprocation. One set 101a-b is in fluid communication with an inner reservoir 131 through reservoir check valves 105 and delivers a specified volume of fluid, e.g., drug 111, at a pre-defined velocity and time interval to the nozzle 103 in a reciprocating manner, e.g., a continuous flow of fluid. The second set of actuators 101c-d can be in communication with an outer concentric reservoir 132 through reservoir check valves 105 and can remove or "suck" exudate and necrotic, damaged, or infected tissue 121 from the wound bed (not shown) though the nozzle 103 via a second pre-defined waveform. This set up can ensure that fluid delivery for debridement and removal of irrigant and wound contents 121 can be performed without interruption.

In operation, the injection actuators 101a-b of FIG. 1D alternate between drawing a debridement substance or fluid 111 from the inner reservoir 131 via check valves 105 and driving the debridement fluid 111 through outflow check valves 106 to continuously drive the debridement fluid 111 into a first section of a coaxial tube 102 and out a nozzle assembly 103 having a nozzle (110 in FIG. 1B). The vacuum actuators 101c-d alternate between supplying negative pressure to a second section of the coaxial tube 102 and driving irrigant and wound contents 121 into an outer reservoir 131 to continuously draw in irrigant and wound contents 121 from a suction port (120 in FIG. 1A) of the nozzle assembly 103. The negative pressure is supplied throughsuction check valves 107 by the vacuum actuators 101c-d during a half cycle of the actuator. During the second half cycle of each vacuum actuator 101c-d, the vacuum actuators 101c-d drive the irrigant and wound contents 121 into the outer reservoir 132. Alternatively, the vacuum actuators 101c-d can be configured to supply a negative pressure to the outer reservoir 132 with the irrigant and wound contents 121 flowing into the reservoir through a single reservoir check valve 105. A controller 140 receives electrical signals from sensors located on the Lorentz-force actuators and on the device handpiece. The controller 140, which may include a microprocessor or personal computer, controls the input waveform to the actuators based on these signals, which may include information about coil position, voltage, current, force transmitted to the fluid, or information from sensors located on the handpiece about the properties of the substance being debrided.

FIG. 1E shows a diagram of the debridement apparatus illustrated in FIG. 1A and alternatively using two of the Lorentz-force actuators 101a, 101c in housing 104 to control the jet and suction. The device 100 of FIG. 1E uses the first (injection) actuator 101a in fluid communication with an inner reservoir 131 through the reservoir check valve 105 to deliver a specified volume of fluid, e.g. drug 111, at a pre-defined velocity and time interval to the nozzle assembly 103 using high frequency pressure pulses. The second (suction) actuator 101c is in communication with an outer concentric reservoir 132 through a reservoir check valve 105. Actuator 101c removes or "sucks" exudate and necrotic, damaged, or infected tissue 121 from the wound bed (not shown) through the nozzle assembly 103 using suction port 120 via pulsed suction. In operation, the injection actuator 101a draws a debridement substance or fluid 111 from the inner reservoir 131 during a half cycle of the actuator. During the second half cycle of the actuator 101a, the actuator 101a drives the debridement fluid 111 though an outflow check valve 106 into a first section of a coaxial tube 102 and out a nozzle assembly 103 having a nozzle (110 in FIG. 1B). The vacuum actuator 101c supplies a negative pressure to a second section of the coaxial tube 102 and to a suction port (120 in FIG. 1A) of the nozzle assembly 103 to draw in irrigant and wound contents 121. The negative pressure is supplied though a suction check valve 107 by the vacuum actuator 101c during a half cycle of the actuator. During the second half cycle of the vacuum actuator 101c, the vacuum actuator 101c drives the irrigant and wound contents 121 into outer reservoir 132. Alternatively, the vacuum actuator 101c can be configured to supply a negative pressure to the outer reservoir 132 with the irrigant and wound contents 121 flowing into the reservoir through a reservoir check valve 105. As with other embodiments, the embodiment shown in FIG. 1E may include a controller 140 that manages sensor signals and generates waveforms for the actuators.

Figure 1F:
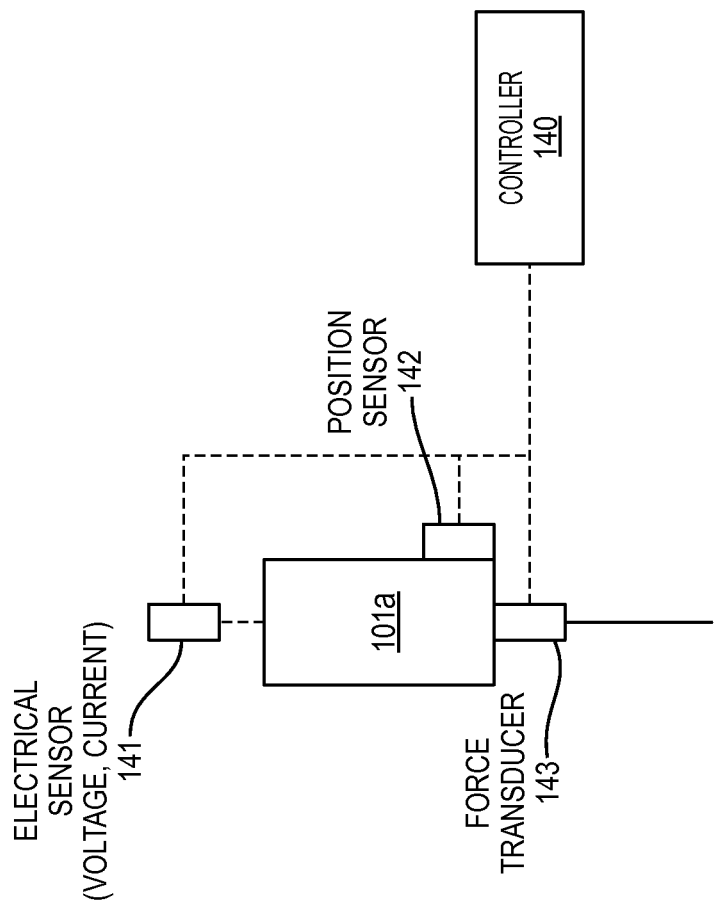
FIG. 1F illustrates an example Lorentz-force electromagnetic actuator and associated sensors.

FIG. 1F shows a more detailed diagram of one of the Lorentz force actuators, and associated sensors 141, 142, 143. A force transducer 143 is mounted at the output of the actuator, where force is applied to the fluid. A position sensor 142 reads coil position, while an electrical sensor 141 measures current through and voltage across the actuator. Signals from each sensor 141, 142, 143 are linked to the controller 140.

FIG. 2A is a cut-away view of a linear Lorentz-force electromagnetic actuator including a moving coil and a stationary magnet assembly. Electromagnetic actuator 201 includes a ferromagnetic shell 222 including a central magnetic core 220 comprising, for example, NdFeB magnets, and is capped by a ferromagnetic end cap 206. A coil assembly 210 is slidably disposed within an annular slot of the magnet assembly floating freely within the slot to drive a plunger 228 into an ampule 208. The stroke of the coil 211 can be controlled by the length of the coil 211 and magnet assembly 220. Thus, the electromagnetic actuator 201 can be configured to transfer a substantial volume of a substance during a single, sustained stroke, .i.e., movement of the coil assembly 210 and by extension the piston or plunger 228 within the ampule 208. The electromagnetic actuator 201 is configured to provide a linear force to the plunger 228 to achieve transfer of a substance through the ampule 208 and into the tubing 102. A negative force pulling the plunger 228 proximally away from the tubing 102 creates a negative pressure or vacuum tending to suck a substance from outside the device 100, through the tubing 102, and into the ampule 208.

In the embodiment shown in FIG. 2B, the actuator 201 is a Lorentz force actuator that includes a stationary component, such as a magnet assembly 220, and a moveable component, such as a coil assembly 210. In more detail, the electromagnetic actuator 201 includes a conducting coil assembly 210 disposed relative to a magnetic field 221, such that an electrical current induced within the coil 211 results in the generation of a corresponding mechanical force. The relationship between the magnetic field, the electrical current and the resulting force is well defined and generally referred to as the Lorentz force law.

Continuing to refer to FIG. 2B, the coil 211 is positioned relative to a magnetic field, such that the magnetic field 221 is directed substantially perpendicular to the direction of one or more turns of the coil 211. Thus, a current induced within the coil 211 in the presence of the magnetic field provided by the magnet assembly 220 results in the generation of a proportional force directed perpendicular to both the magnetic field and the coil 211. The force produced within the coil assembly 210 can be applied to the plunger 228 either directly or indirectly through the rod 228 to achieve transfer of the substance. The mechanical force is capable of moving the coil assembly 210 and exerting work on the plunger 228 of the ampule 208 to, for example, drive a fluid from ampule 228 and into the tubing 102. The Lorentz-force actuator 201 can include a displacement transducer 240 to provide feedback for controlling the position of the plunger 228 and the flow rate of a substance through the tubing 102.

The distal end of the shell 222 includes one or more extensions 224 that continue proximally from the distal end of the shell 222 and terminate at the distal mounting plate 212. The interior surface of the shell 222 including its extensions 224 provide a bearing surface for the coil assembly 210 allowing axial movement while inhibiting radial movement. A first bearing surface 250 is defined along a distal end of the coil assembly 210. The first bearing surface 250 slides against the interior surface of the extensions 224 during actuation. A second bearing surface 255 is provided at a proximal portion of the coil assembly 210 and slides against the interior surface of the shell 222 during actuation.

The extensions 224 may include openings between adjacent extensions 224 as shown to reduce weight, permit the flow of air to promote coil 211 movement, and allow cooling. This configuration 201 rigidly couples the distal mounting plate 212 to the shell 222, thereby increasing rigidity of the actuator 201 and reducing if not substantially eliminating any stress/strain loading on the housing 104 (FIG. 1) caused by actuation of the device 201.

Figure 3B:
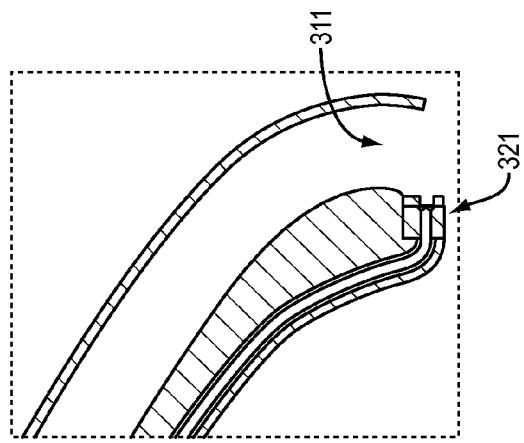
FIGS. 3A-B are views of an example embodiment of a hand piece of a debridement apparatus.
Figure 3A:
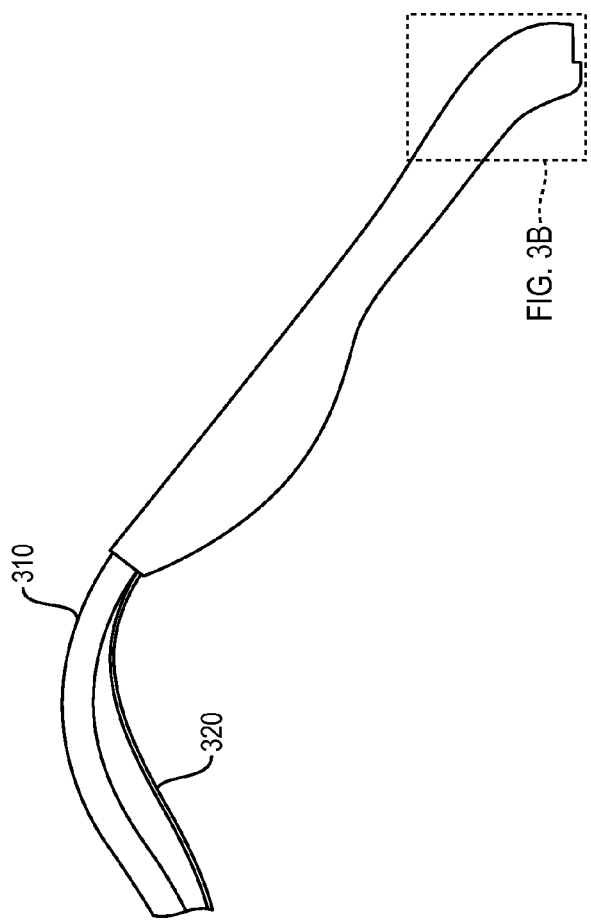

FIG. 3A is a view of an embodiment of the hand piece of the device illustrated in FIG. 1, which contains the tubing used to deliver fluid at variable pressure (velocity) to the wound bed, the evacuation tubing for removal of exudate and necrotic, damaged, or infected tissue from the wound bed, and the nozzle assembly and evacuation lumen. FIG. 3B is a detailed view of the distal end of the device illustrated in FIG. 3A. Evacuation tubing 310 supplies a negative pressure to an evacuation lumen 311 and a variable pressure inflow tube 320 delivers a fluid at variable pressures to a nozzle 321 adjacent to the evacuation lumen 311. The evacuation lumen 311 removes tissues separated from a wound bed (not shown) by the nozzle 321.

FIG. 4A is a view of an embodiment of the present invention showing the hand piece of the device which contains the tubing used to deliver fluid at variable pressure (velocity) to the wound bed, the evacuation tubing for removal of exudate and necrotic, damaged, or infected tissue from the wound bed, the nozzle assembly and evacuation lumen, and an additional tube that delivers fluid under low pressure (velocity) to control the distance over which the fluid exiting the nozzle cuts. FIG. 4B is a detailed view of the distal end of the device illustrated in FIG. 4A. Evacuation tubing 410 supplies a negative pressure to an evacuation lumen 411 and a variable pressure inflow tube 420 delivers a fluid at variable pressures to a nozzle 421 adjacent to the evacuation lumen 411. The evacuation lumen 411 removes tissues separated from a wound bed (not shown) by the nozzle 421. A low-pressure inflow tube 430 supplies fluid under low pressure (velocity) to the tissue. In some situations, this jet serves to control the depth of penetration of the fluid exiting the nozzle 421 by intersecting the cutting jet causing it to lose momentum. In other situations, the low velocity jet lavages the tissue (not shown).

FIGS. 5A-C are isometric views of a nozzle assembly. FIG. 5A shows the nozzle core 500 housing the high-pressure lumen 501. FIG. 5B shows the slit 504 created following insertion of two longitudinal rods 502 that together with the diameter of the high-pressure lumen 501 define the nozzle orifice 504 through which the fluid is ejected at a user defined velocity (pressure). In addition, FIG. 5C shows the nozzle 500 following the addition of a front plate 503 that is used to secure the rods and contains an opening 505 for fluid ejection, the opening being larger than that of the high-pressure lumen 501. Changing the spacing between the rods 502 permits the height of the slit 504 to be varied in a controlled manner. Changing the diameter of the high-pressure lumen 501 can be used to alter the width of the slit 504 while changing the geometry of the front plate 503 can affect the dispersion of the fluid after it exits the nozzle orifice 504.

Figure 6B:
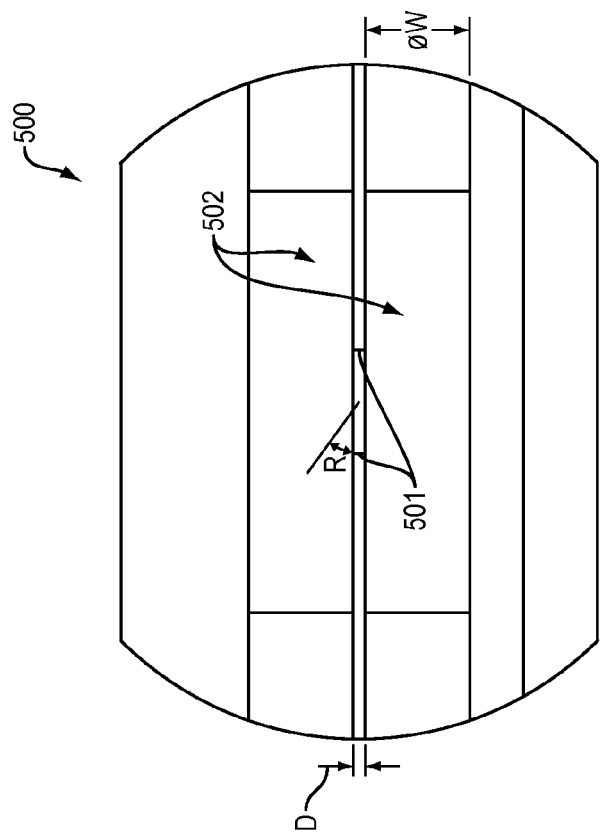
FIGS. 6A-B are respective sectional and front views of a nozzle assembly prior to addition of the front plate.
Figure 6A:
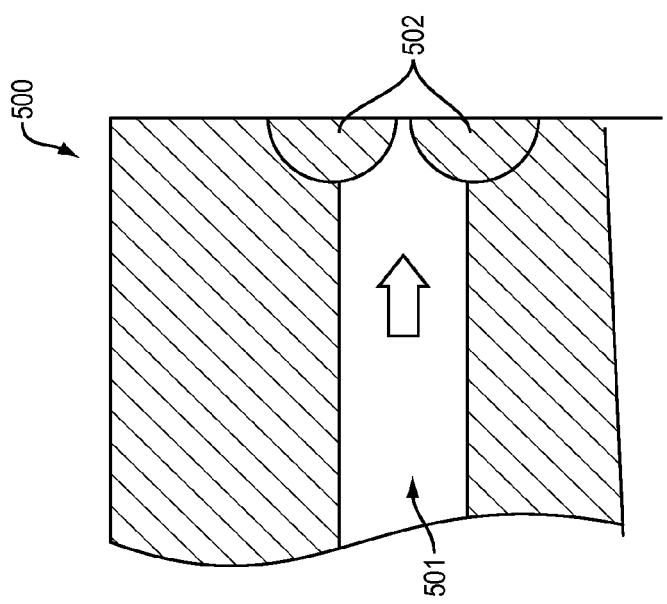

FIG. 6A shows a cross-sectional side view of a nozzle assembly illustrated in FIG. 5B showing the high-pressure lumen 501 and the placement of the rods 502 in the lumen 501 and wall of the core housing 500. Shown is a lumen 501 and rods 502 of similar diameter and a nozzle or slit orifice of 0.1 mm (D in FIG. 6B). The arrow in the lumen 501 shows the direction of fluid flow.

FIG. 6B shows the front view of the nozzle assembly shown in FIG. 6A. The lumen 501 is shown here to have a radius of curvature (R) of 0.5 mm while the slit 504 is shown to have a height (H) of 0.1 mm and width defined by the diameter of the lumen 501. The rods (502 in FIG. 6A) do not extend to the outside walls of the core nozzle housing 500.

FIG. 7A shows a cross-sectional side view of a nozzle assembly illustrated in FIG. 5C showing the high-pressure lumen 501, the placement of the rods 502 in the lumen 501 and wall of the core housing 500, and the positioning of a front plate containing an opening to permit fluid ejection. In the illustration, the front plate 503 shown has a depth (H) of 1 mm and secures the rods 502 to the housing 503. The arrow in the lumen 501 shows the direction of fluid flow.

FIG. 7B shows a front view of the nozzle assembly illustrated in FIG. 7A. In the example shown, the opening 505 in the front plate 503 has a radius of curvature (R) of 0.5 mm and a diameter (L) of 1.5 mm. The lumen 501 and distance between the rods which together define the nozzle orifice 504 are shown here to be 1.0 mm wide and 0.1 mm in height (H), respectively.

FIG. 8 is a view of a debridement device embodiment showing a hand piece with a first and second nozzle orifice. Fluid from a high-pressure source, e.g., pump or other actuator described herein, is driven through a high-pressure hose and into the hand piece for ejection through the nozzles. The debridement device 800, shown in FIG. 8, includes hand piece 801 having a lumen in fluid communication with the high pressure hose 803, the lumen in the hand piece being contiguous with the fluid channels in each elbow fixture and nozzle adaptor together referred to as the nozzle arms 804 a-b, each nozzle arm terminating in a nozzles 805a-b through which fluid or slurry is ejected. In this embodiment, variable fluid pressure can be achieved by increasing or decreasing the air pressure to a pneumatic piston pump or by controlling the electrical input signal to an electromagnetic fluid actuator in fluid communication with the high pressure hose 803.

Figure 9C:
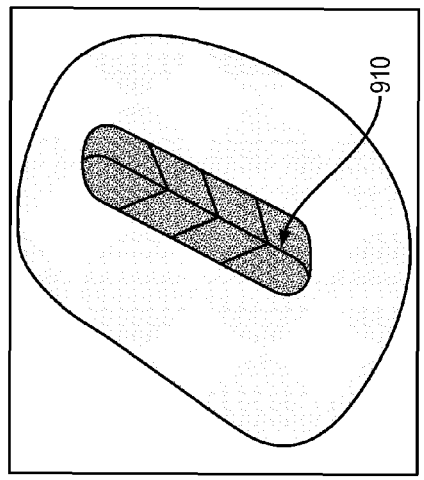
FIGS. 9A-C are schematic illustrations showing an example sequence of tissue removal using two nozzles.
Figure 9B:
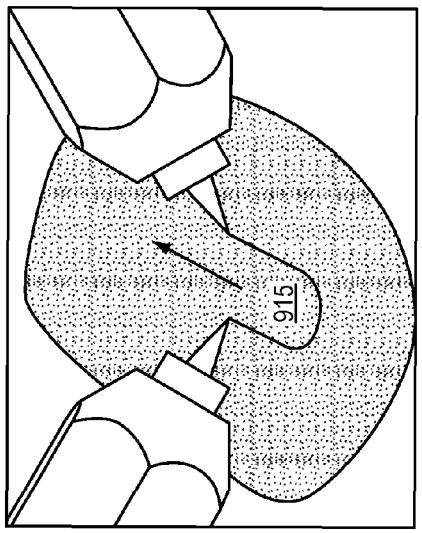
Figure 9A:
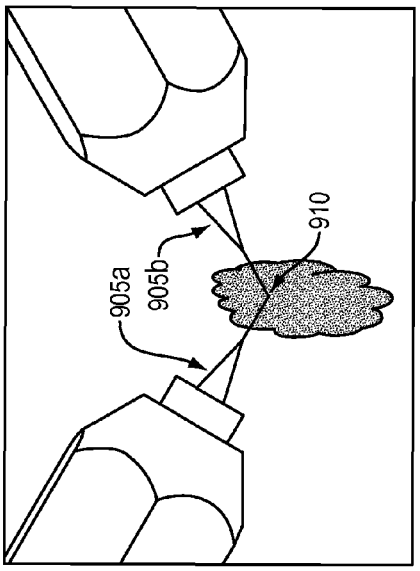

FIGS. 9A-C are schematic illustrations showing an example sequence of tissue removal using a first and second nozzle. The two nozzles 905a-b are directed so that the ejected fluid from each exactly intersects, as shown in FIG. 9A. The impinging jets dissipate into a mist upon intersection 910. The mist retains a small fraction of the kinetic energy of the jets. When directed into tissue, the jets have enough energy to cut, while the mist does not. Thus, when the nozzles are held at the wound surface and moved laterally, as in 9B, the two jets cut and separate a distinct section of tissue 915, but there is no cutting beyond the intersection line 910, as shown in FIG. 9C.

FIGS. 10A-B are perspective and section views, respectively, of an example hand piece with first and second nozzles and a cross section through the hand piece showing the composition of each nozzle, the O-ring seal, and the fluid flow from the tubing through each nozzle. In the embodiment shown in FIG. 10A-B, the distance and angle between the nozzles 1005a-b is adjustable. Each nozzle 1005a-b is held via a threaded adaptor to an elbow fixture 1004, referred to as the nozzle arm. Each nozzle arm 1004 is threaded into a separate block 1008, 1009. The angle of each nozzle orifice 1005a-b can be adjusted relative to the other by rotating the nozzle arms 1004 in a fixed plane to yield variable intersection angles. The distance between the blocks 1009, 1008 is adjusted with a lead screw 1007, which controls the translation of block 1008 via the engagement of an extended point set screw 1010 in the groove 1011 at the proximal end of the lead screw 1007. This permits the nozzle-containing block 1008 to move towards or away from the fixed block 1009 that contains the second nozzle. A pipe 1015 extends between the two blocks 1008, 1009 permitting the flow of water to each of the nozzles 1005a-b. An O-ring 1012 maintains a watertight seal for all configurations. A bottom plate 1013 and top rod (1014; shown in FIG. 10A but not FIG. 10B) serve to balance the separating force exerted by the pressurized fluid on blocks 1008 and 1009, keeping the two blocks separated by the distance dictated by the lead screw 1007.

Figure 11B:
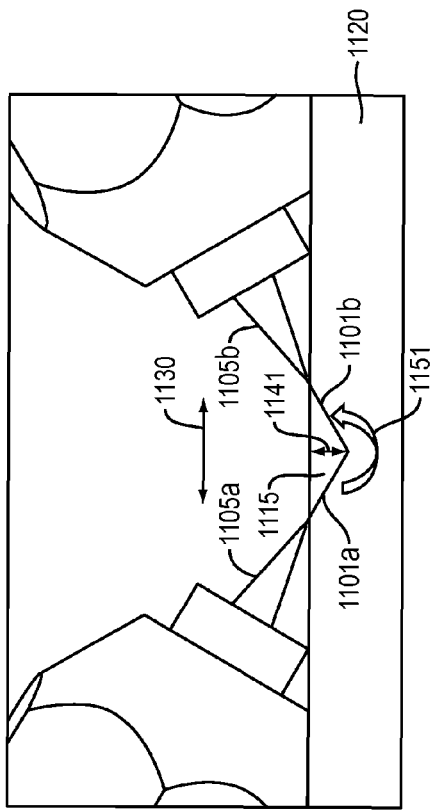
FIGS. 11A-B illustrate how angle and distance between the nozzles affect the cross section of tissue removed.
Figure 11A:
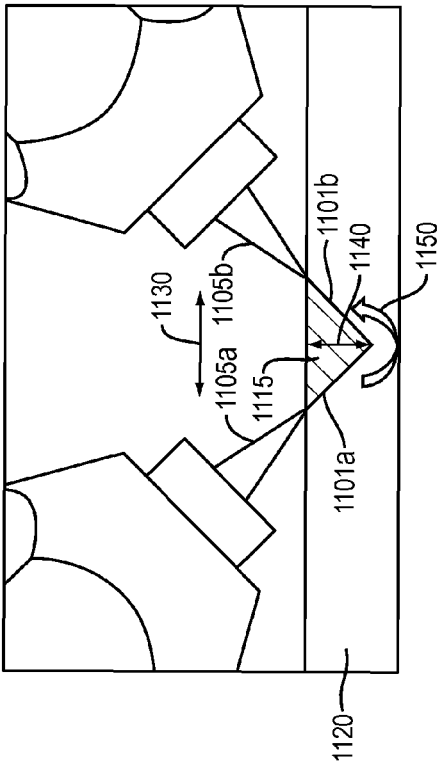

FIGS. 11A-B illustrate how nozzle angle and distance between the nozzles affect the cross section of tissue removed. When in use, the jets 1101a-b are moved laterally, excising a section of necrotic tissue of predetermined depth 1140 and width 1130. In FIG. 11A, the user-defined nozzle 1105a-b intersection angle 1150 (shown as 90 degrees) together with the separation distance between the nozzles (shown as 4 mm) determines the point of intersection of the two jets 1101a-b. When the jets are of comparable velocity, the dissipation of energy at the point of intersection results in the creation of a mist thereby preventing further cutting of the tissue 1120. In FIG. 11B, while the distance between the nozzles is unchanged (shown as 4 mm), the jets the jets 1101a-b are positioned at a different angle 1151 (shown as 120 degrees) which results in a different cutting depth 1141 but comparable cutting width 1130 as that illustrated in FIG. 11A.

Referring to FIGS. 11A and 11B, the volumetric flow rate of the device varies as a function of fluid pressure and diameter of the nozzles 1105a-b. The pressure required to cut ranges from 2 to 20 MPa and depends on the properties of the tissue 1120 being debrided as well as the distance between and angle 1150, 1151 of the nozzles 1105a-b. The nozzle diameter is in the range of 50-100 μm. At a pressure of 15 MPa using a 75 μm nozzle, the device would have a flow rate of 1.5 mL/s.

FIGS. 12A-B illustrate an example embodiment of a debridement device that includes a surgical blade mounted in the proximity of each nozzle to score the tissue prior to tissue cutting and removal using the liquid jets. High-pressure jets can drive bacteria and other contaminants deeper into the wound bed as well as inject water into the tissue. Lowering the cutting pressure can mitigate these effects. In order to reduce requisite cutting pressure, a surgical blade 1216a can be used to score the tissue prior to cutting. In this embodiment, shown in FIG. 12A, a small blade 1216a is positioned adjacent to the nozzle 1205a and as the hand piece is moved across the tissue in the direction of the arrow shown, the blade 1216a slices the tissue 1215 which is immediately followed by cutting of the tissue at the scored site by the fluid jet exiting the nozzle 1205a. The blade 1216a can be mounted in series with a load cell 1245 that can determine the cutting force. Cutting can be enhanced by vibration from a piezo actuator 1244. In combination, the load cell and piezo actuator can provide a measure of mechanical impedance. Shown in FIG. 12B, the blades 1216a-b are mounted adjacent to respective nozzles 1215a-b in receptacles/covers 1217a-b made from moldable synthetic or semi-synthetic organic solids that mount to and cover the existing nozzle hardware. The arrow denotes the direction of movement. Each blade 1216 can serve as an electrode for determination of electrical impedance, an indicator of tissue scoring and depth. Both the blades and covers are disposable.

Figure 13A:
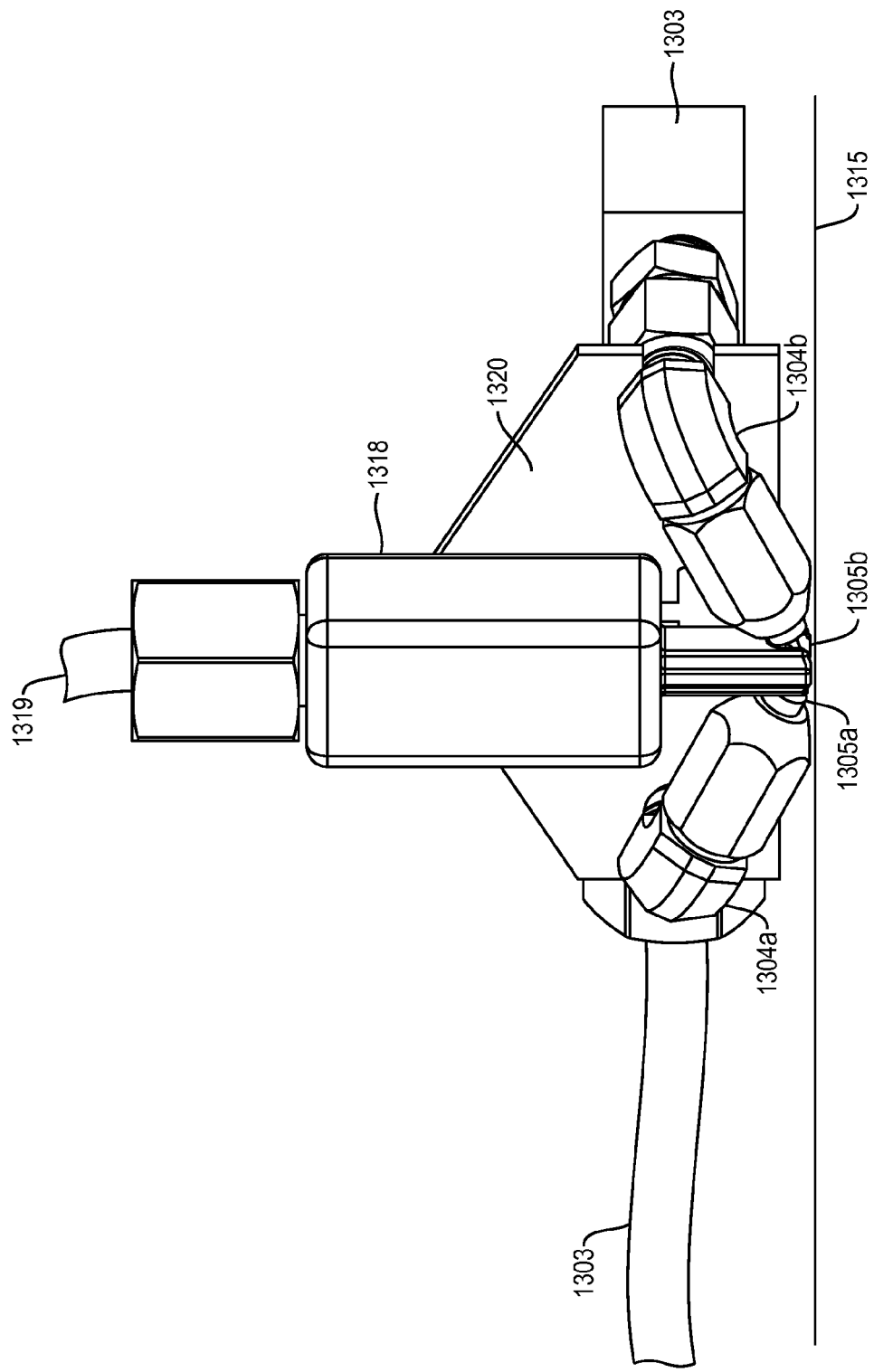
FIGS. 13A-B are respective front and partial sectional views of an example debridement device that includes a vacuum to permit the removal of dead, damaged, or infected tissue or exudate.
Figure 13B:
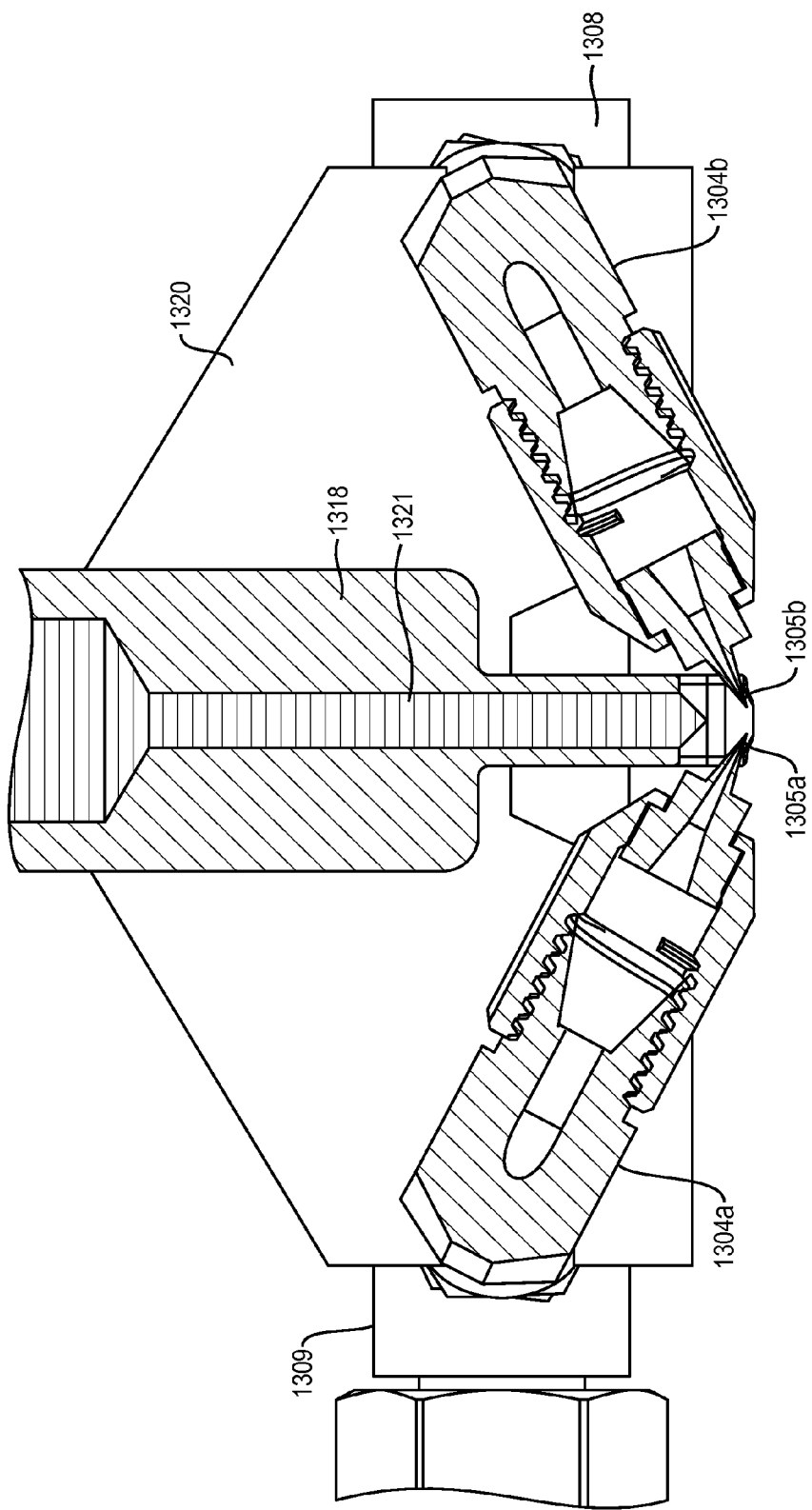

FIGS. 13A-B are respective front and partial sectional views of an example debridement device that includes a vacuum to permit the removal of dead, damaged, or infected tissue or exudate. Effective debridement requires that the necrotic skin, tissue, contaminants, and excess exudate be removed from the wound bed leaving behind viable undamaged tissue. This can be accomplished by creating a vacuum chamber capable of sucking the debrided material from the site as shown in FIGS. 13A-C; sucking can be accomplished using the Lorentz-force actuator as discussed above or by attaching an alternative vacuum source to the device. An evacuation chamber (also referred to as a vacuum attachment) 1318 is placed between the two nozzles 1305a-b such that the border of the lower end of the vacuum chamber 1318 touches the wound bed surface 1315, both stabilizing the tissue for cutting and also removing debrided tissue, contaminants, and exudate using an evacuation lumen 1319.

The vacuum attachment 1318 mounts to a plate 1320, which in turn mounts to the existing hardware, for example, the hand piece 1303 and nozzle arms 1304a-b.

FIG. 13B is a cross section view of the vacuum channel, nozzle arms, and nozzles. A cross sectional view of the evacuation chamber 1318, vacuum channel 1321, nozzle arms 1304a-b, and nozzles 1305a-b is shown in FIG. 13B. The nozzles 1305a-b are seated into an adaptor housing threaded into an elbow fitting which together constitute the nozzle arms 1304a-b, with the interfaces made liquid-tight (e.g., watertight) using compression fittings consisting of acrylic crush washers. The distal tips of the nozzles 1305a-b are shown to protrude into a cavity or slot created in the end of the evacuation chamber 1318, which places the tips within but not touching the vacuum channel 1321. As shown more clearly in FIGS. 14A-C, this cavity or slot shields the area around the nozzles, focusing the vacuum in the cutting area. The attachment does not directly contact the nozzles 1305a-b.

FIGS. 14A-C show enlarged views of the vacuum channel and the relative position of the nozzle arms, and nozzle jets with respect to the vacuum chamber of the device illustrated in FIG. 13A. FIG. 14A is a detailed, partial sectional view of the evacuation chamber 1318 and nozzle arm 1304b. The nozzle 1305b extends into the cavity or slot 1422 in the evacuation chamber 1318 at the distal end of the vacuum channel 1321. As shown, the vacuum chamber 1318 can optionally house a port 1447 in which a sensor 1446, such as a near IR, SERS, and/or optical sensor, can be seated. The bottom up view represented in FIG. 14B shows the cavity or slot 1422. In addition, it shows that the vacuum attachment 1318 narrows at the front and back to form a 2 mm ridge 1423, equal to the distance between the nozzles 1305a-b. This feature provides the user with a fixed navigation tool for placement of the nozzles 1305a-b over the region of tissue requiring debridement. A top down view of the same navigation ridges 1423 and position of the nozzles 1305a-b relative to the vacuum attachment 1418 is shown in FIG. 14B.

While the inclusion of the surgical blades and vacuum as components of the debridement device have been discussed separately, they can easily be combined into a single device.

Figure 15:
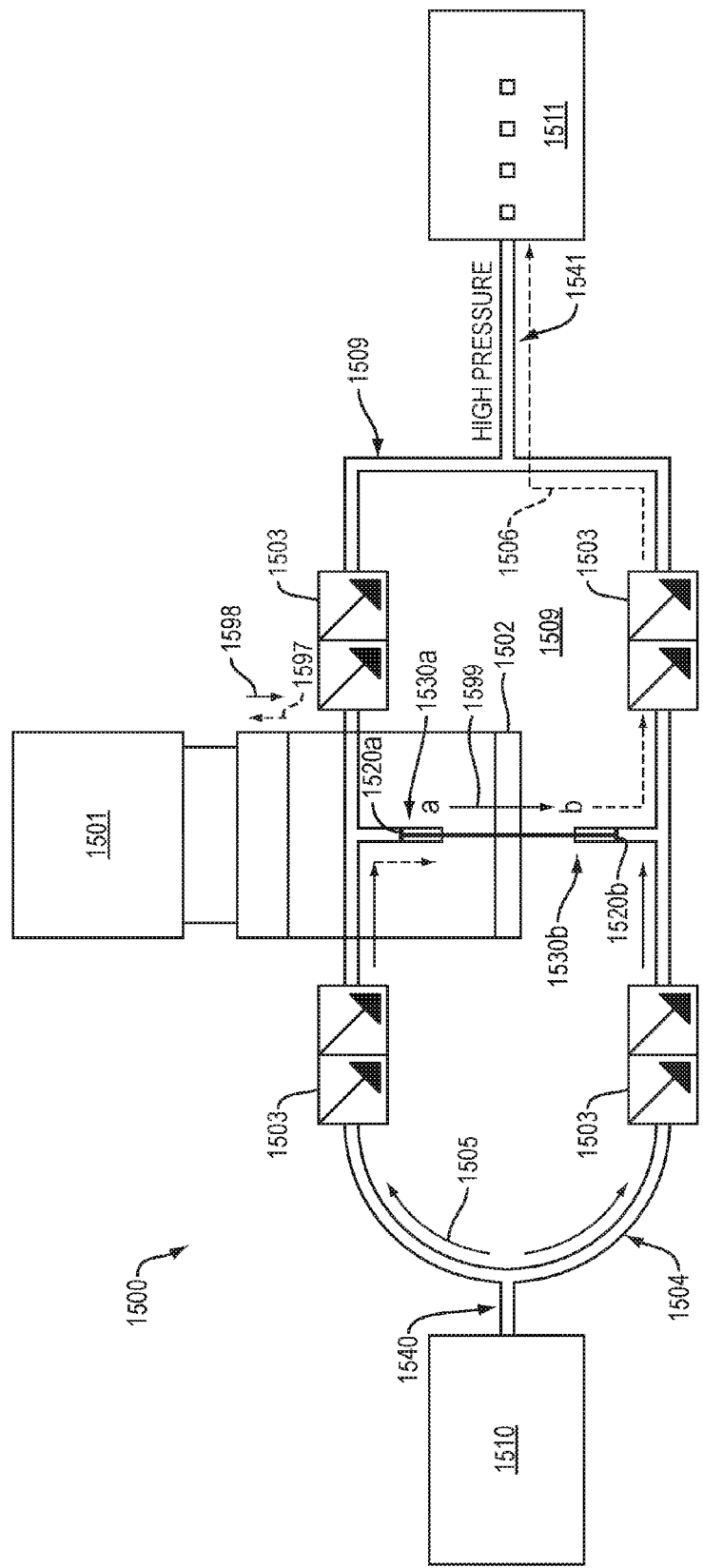
FIG. 15 is a diagram illustrating a design for continuous delivery of debridement solution to a wound bed.

FIG. 15 is a diagram illustrating the operation of an embodiment enabling continuous delivery of debridement solution to a debridement nozzle unit. The reciprocating pump system 1500 of FIG. 15 may be employed, for example, to drive debridement solution to the debridement device 800 shown in FIG. 8. Fluid from a low pressure reservoir 1510 permeates the tubing 1504 forming the circuit between low and high pressure flow. Direction of flow 1505 is restricted using backflow prevention valves 1503. Reciprocating movement of the pistons 1520a, 1520b ensures continuous flow. Arrow 1599 and dotted lines 1506 denote the direction of piston 1520a, 1520b movement and fluid flow respectively when the direction of current input to the voice coil of a linear Lorentz-force motor 1501 results in forward motion (black arrow 1598) of the motor 1501; the opposite would occur when the motor 1501 moves in the reverse direction (black dotted arrow 1597).

In the embodiment illustrated in FIG. 15, a single linear Lorentz-force motor 1501 is coupled to a rigid, reciprocal piston assembly 1502 to deliver fluid continuously to the wound bed (1120 in FIG. 11A). A solution in a low pressure reservoir 1510 supplies a fluid circuit (e.g., tubing 1504) between a low pressure inlet 1540 and a high pressure outlet 1541. This fluid circuit includes backflow prevention valves 1503, each comprised of two check valves in series (indicated by black arrows). Two back-to-back pistons 1520a, 1520b coupled to the linear Lorentz-force motor 1501 move in reciprocal motion 1598 to draw fluid from the low pressure reservoir 1510 and then to drive the fluid at high pressure into a high pressure outlet 1541 connected to the handpiece 1511 for ejection through one or more nozzles (1105a,b in FIG. 11A). The fluid pressure may be varied by increasing or decreasing the voltage (current) used to drive the linear Lorentz-force motor 1501.

More specifically, actuation of the piston assembly 1502 in the forward direction 1599 causes piston A 1520a and piston B 1520b to be driven forward 1599. This forward movement results in the fluid in the central compartment 1530b (into which piston B 1520b moves) to be driven across the backflow prevention valve 1503 and into the high pressure hose (direction of flow indicated by dotted lines 1506), which leads to the handpiece 1511 for delivery. The check valves 1503 between this central chamber 1530a,b and the low pressure reservoir 1510 prevent backflow. As the actuator 1501 drives piston A 1520a forward, the pressure in the central chamber on that side 1530a decreases, drawing additional solution from the low pressure reservoir 1510 across the valve 1503 and into the compartment 1530a. Switching the direction of current pulls piston B 1520b and piston A 1520a toward the actuator 1501, driving fluid in the opposite direction with the same result: high pressure fluid is driven into a high pressure hose 1541 connected to the handpiece 1511. The dual piston assembly 1502 in this embodiment enables a smoother pressure profile when compared to a pneumatically actuated device where the pressure dropped during a refill phase.

Figure 16:
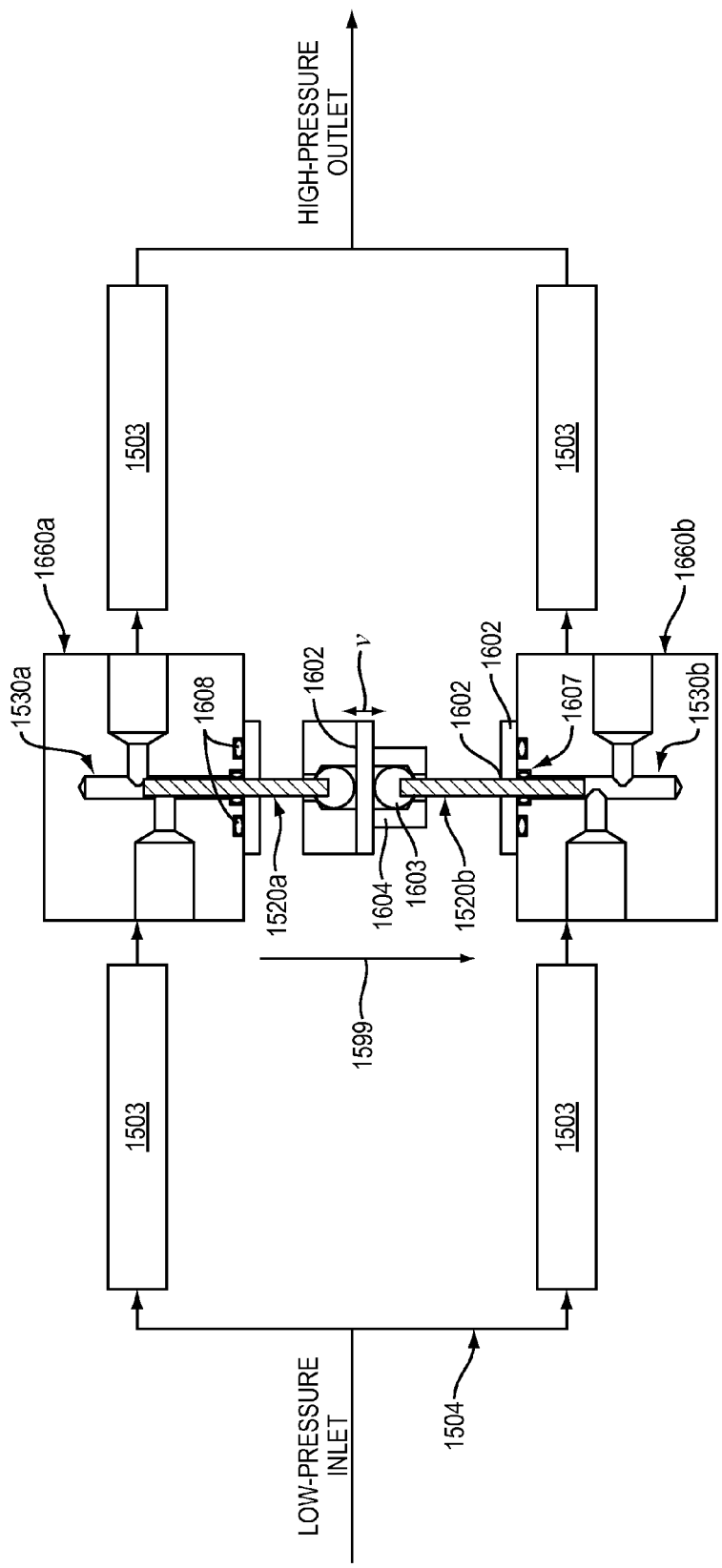
FIG. 16 is a schematic illustrating a cross-section of the internal components of a device having aspects of the embodiment illustrated in FIG. 15.

FIG. 16 is a schematic illustration of a cross-section of the internal components of the embodiment illustrated in FIG. 15. As the piston assembly 1502 moves (direction shown by arrow 1599), piston B 5120b is driven to the end of its stroke blocking the leftmost inlet and solution can only move through the tubing to the outlet. The decrease in pressure created in the complementary compartment holding piston A 1520a results in solution being drawn from the inlet reservoir into this compartment thereby filling it again. When the direction of the stroke is reversed, a similar series of events occur but in the opposite direction. A spring-actuated seal collars the piston preventing leakage.

Figure 17:
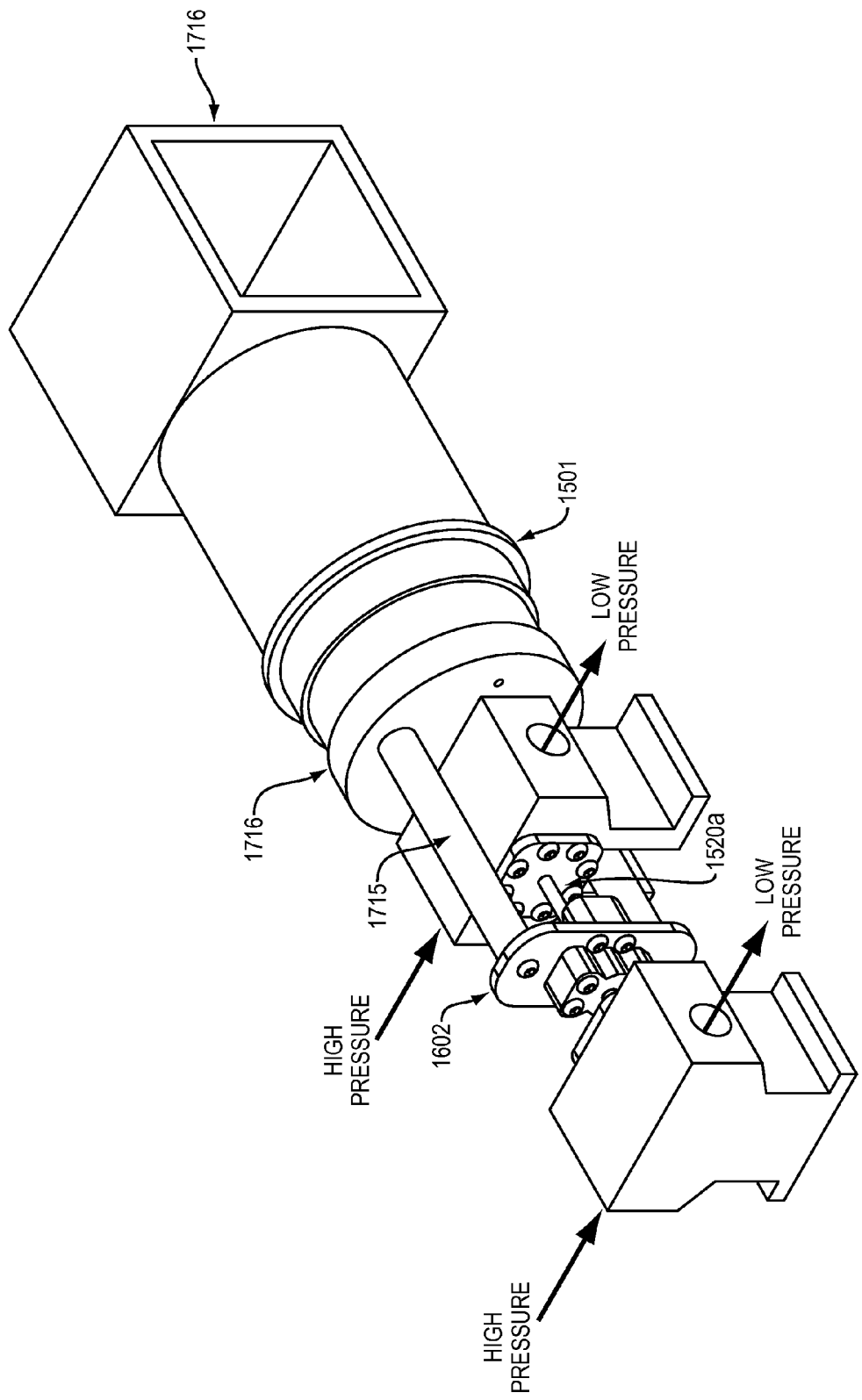
FIG. 17 is a rendering illustrating a device having an attachment of a center plate-piston assembly to a motor output.

In this embodiment, force is transferred to the back-to-back pistons 1520a,b via an aluminum plate 1602, which is offset from the actuator 1501 by two aluminum rods (shown as 1715 in FIG. 17). Each piston 1520a,b may be screwed into a stainless steel ball 1603, which is in turn secured to the center plate 1602 by a retaining block 1604. The use of these spheres 1603 compensates for misalignment and prevents over-constraint. Each piston 1520a,b interacts with the fluid circuit 1504 through a tightly-toleranced orifice 1602, providing the piston access to the central chamber 1530a,b between the backflow prevention valves 1503. The piston 1520a,b moves reciprocally through the hole 1602, drawing in fluid or forcing it out of the central chamber 1530a,b. The connection may be sealed by a spring-actuated PTFE shaft seal 1607. When used in a seal, the canted-coil spring 1607 offers two advantages: it has lower friction than an O-ring, and also the force of the canted-coil spring 1607 remains relatively constant within the working deflection, providing an effective seal that compensates for wear and mating tolerance thereby preventing leakage. An O-ring 1608 may surround the shaft seal 1607 and create a face seal between the plate 1602 and the pump unit 1660a,b also to prevent leakage.

FIG. 17 is a rendering illustrating a device having an attachment of a center plate-piston assembly to a motor output. The center platform 1602, to which the back-to-back pistons 1520a,b are secured, is attached to the actuator 1501 via two cylinders 1715 protruding from the front face of the moving coil 1716 of the actuator 1501. Input to the coil 1716 results in two-way (forward and reverse) movement of the rods 1715 and, by extension, the piston assembly plate 1602. An inductive position sensor (not shown) monitoring the position of the coil 1716 may be mounted in a mounting block 1716 behind the voice coil actuator 1501.

Figure 18B:
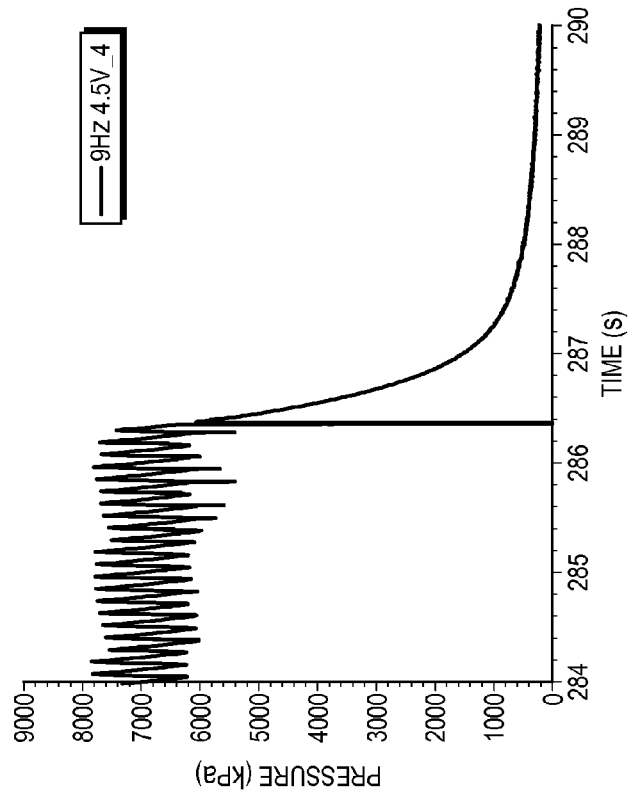
FIG. 18B is a graph showing the fluid capacitance of a system having aspects of the embodiment shown in FIG. 15.
Figure 18A:
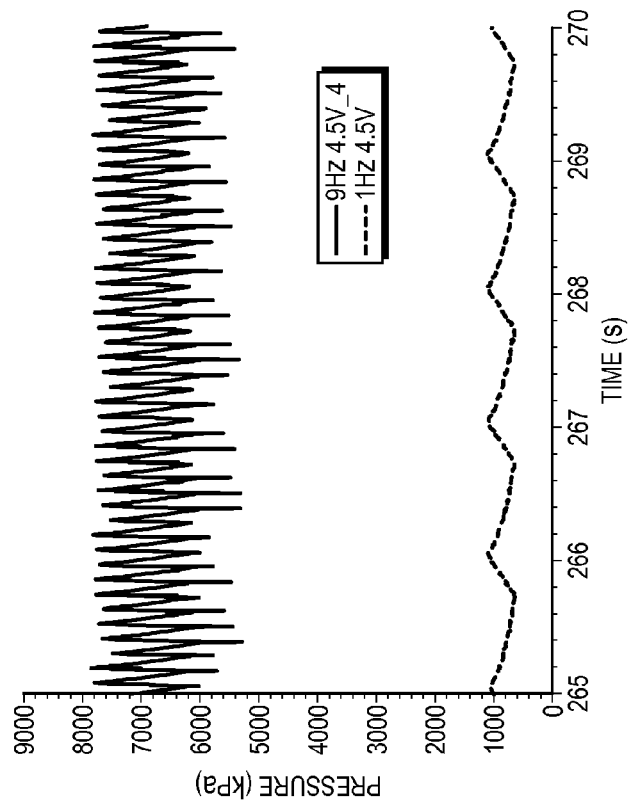
FIG. 18A is a graph showing change in pressure as a function of time of a system having aspects of the embodiment shown in FIG. 15.

FIG. 18A is a graph showing change in pressure as a function of time of a system having aspects of the reciprocating pump embodiment shown in FIG. 15. FIG. 18A shows change in pressure as a function of time, with higher pressures generated for higher frequency pumping; 1 Hz and 9 Hz pressure profiles were input to the actuator 1501 generating the two profiles shown. Position (closed loop), pressure, and voltage output from the motor are controlled. The pump system 1500 providing the data of FIG. 18A is shown to provide a relatively steady flow at specified pressures with the upper range being consistent with that required for debridement. As shown, the system 1500 is capable of maintaining a constant pressure within a range of 2 MPa.

FIG. 18B is a graph showing the fluid capacitance of a system having aspects of the embodiment shown in FIG. 15. When current input to the voice coil 1716 of the actuator 1501 is removed, after the 286 second mark, the pressure decays exponentially demonstrating the fluid capacitance of the system 1500. The fluid capacitance during normal operation allows the system 1500 to maintain elevated pressures even when the actuator 1501 reverses direction and is not instantaneously supplying pressure. This capacitance ensures a continuity of flow which allows for predictable debridement.

Figure 19:
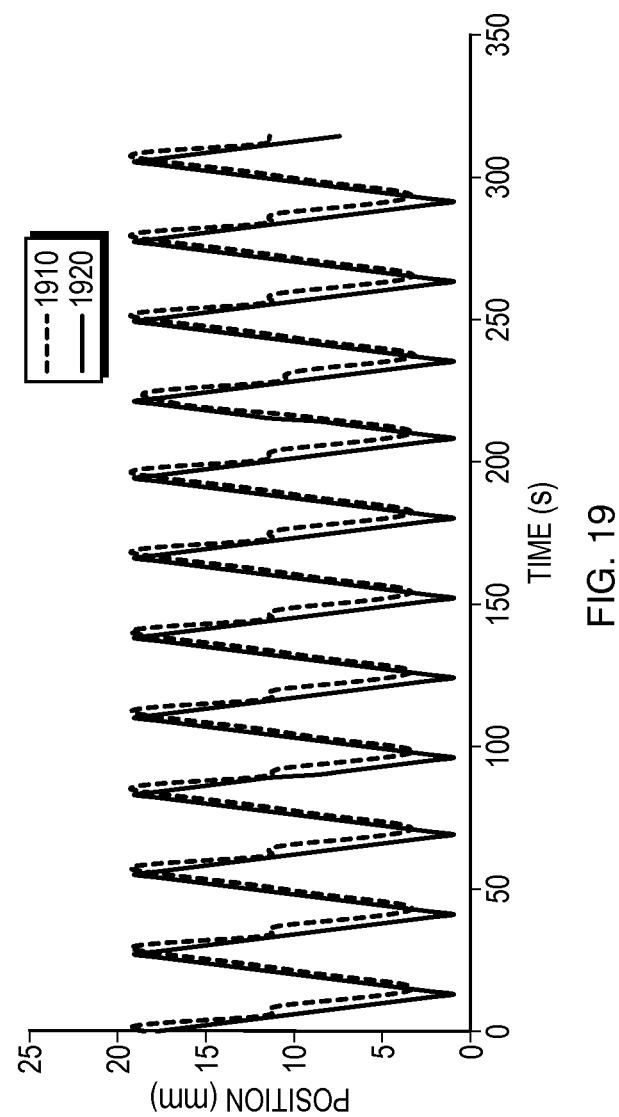
FIG. 19 is a graph of the voltage commanded vs. measured piston position of a system having aspects of the embodiment shown in FIG. 15.

FIG. 19 is a graph of fit between the commanded vs. measured piston position of a system 1500 having aspects of the embodiment shown in FIG. 15. Closed loop position control of the reciprocating piston pump system 1500 is demonstrated in FIG. 19. Commanding a triangle wave, as shown by the solid line plot of commanded piston position 1920 (representing 4.5 volts at 9 Hz), approximates continuous linear motion at a constant velocity of the measured piston 1530a,b position, as shown by the dotted line 1910.

Figure 20:
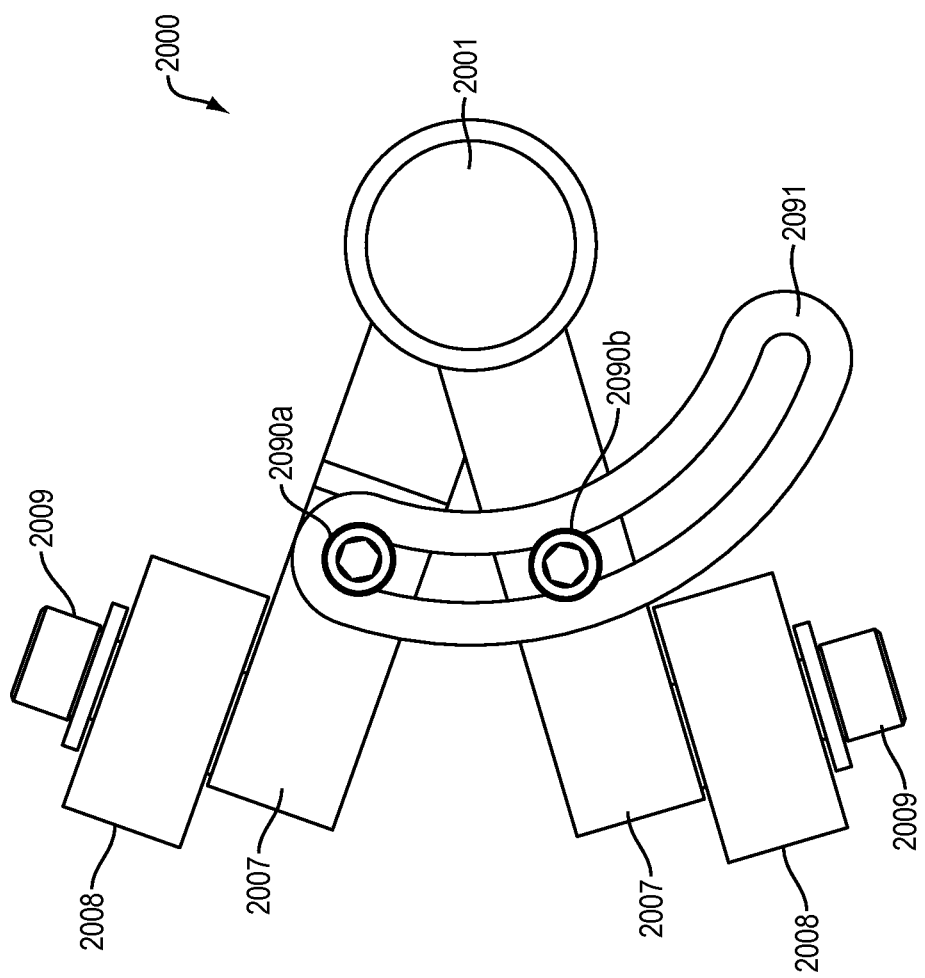
FIG. 20 is a schematic illustrating a tissue tensioner embodiment.

FIG. 20 is a schematic illustrating a tissue tensioner according to aspects of the disclosed embodiments. A tissue tensioner 2000 includes a pivot joint 2001 connecting two arms 2007 together. Each arm 2007 supports a wheel 2008 secured by a bearing 2009 to the arm. The arms 2007 include adjustment bolts 2090a,b traveling alone an angular adjustment race 2091. The bolts 2090a,b being positioned at different points along the race 2091 enables the arms 2007 and wheels 2008 to be positioned at a desired angle with respect to each other.

Figure 21:
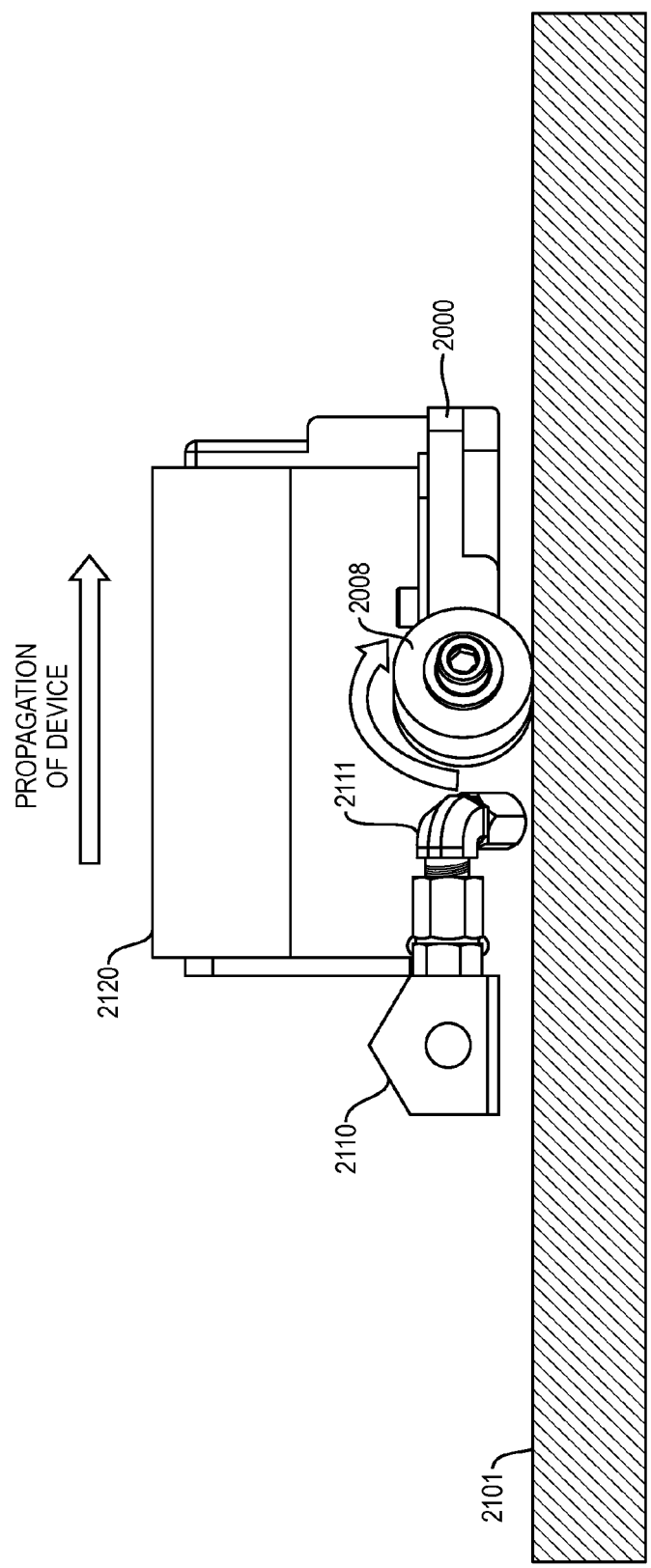
FIG. 21 is a schematic illustrating a hand piece including a tissue tensioner and a dual nozzle debridement device.

FIG. 21 is a schematic illustrating hand piece embodiment having a tissue tensioner and a dual nozzle debridement device. A tissue tensioner 2000 and a debridement device 2110 are connected to a handle 2120. The debridement device 2110 includes a nozzle assembly 2111 configured to deliver a jet a debridement solution to a region of target tissue 2101. In operation, movement of the handle 2120 moves the nozzles of the debridement device 2110 across the tissue 2101 and rolls the wheels 2008 of the tissue tensioner 2000 across the tissue 2101 in advance of the debridement device 2110.

Figure 22:
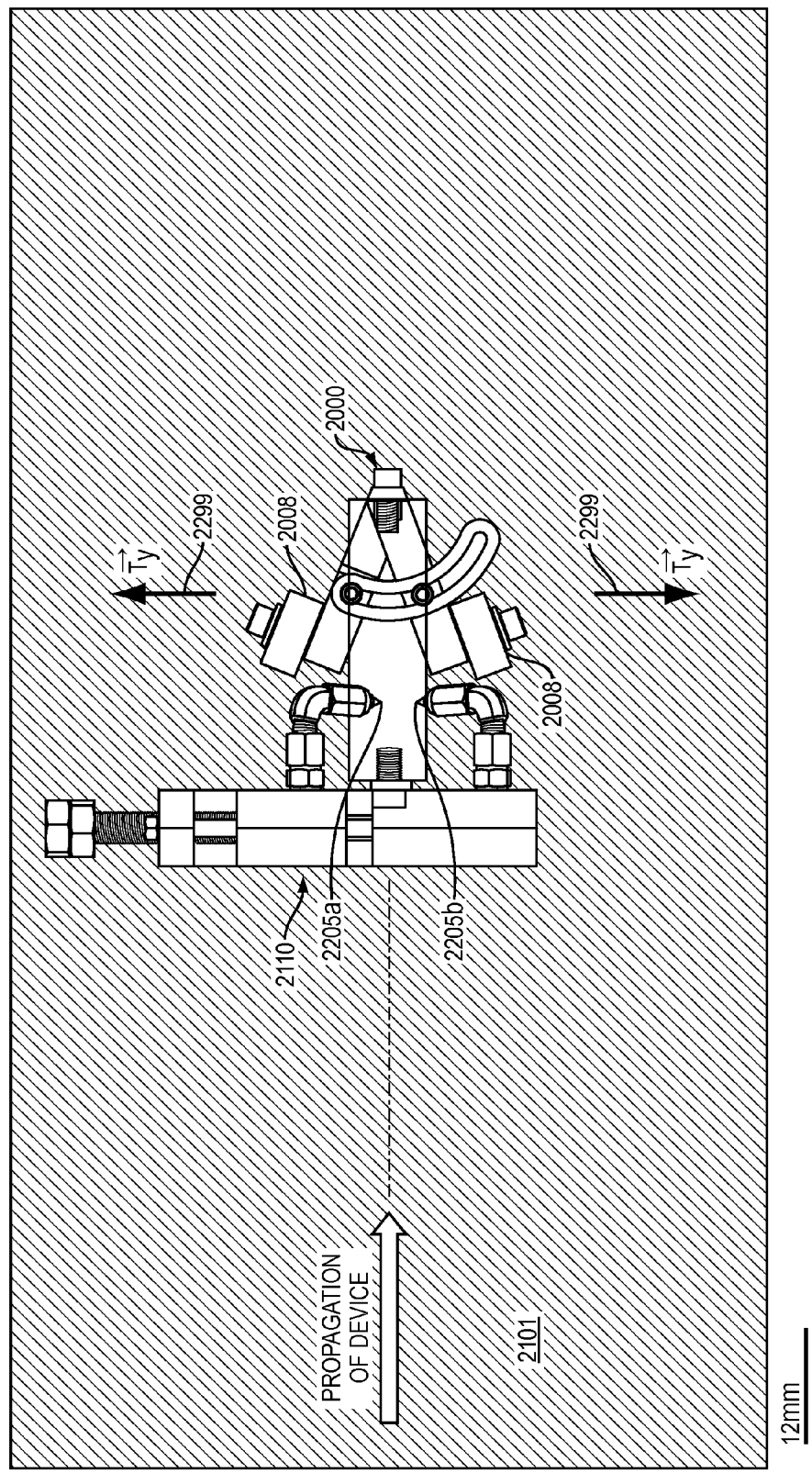
FIG. 22 is a schematic illustrating a top-down view of the hand piece of FIG. 21.

FIG. 22 is a schematic illustrating a top-down view of the hand piece of FIG. 21. In one configuration, two wheels 2008 roll along the tissue surface 2101 and deliver tension forces 2299 to the area impacted by the cutting jets 2205a,b. Tension 2299 has been shown to reduce the required cutting pressure. The wheels 2008 flank the cutting nozzles 2205a,b and are offset slightly ahead of the nozzles 2205a,b. The surface of the wheel 2008 comes into contact with the tissue surface 2101 ahead of the cutting zone, and rolling contact is maintained with that same spot on the tissue 2101 until it is even with the cutting zone. The wheels 2008 are angled so that the forward edges of the two wheels 2008 are closer together than the back end. Thus, as the wheels 2008 maintain contact with a particular spot on the tissue 2101 (wound bed) through the roll, the section of tissue 2101 is tensioned between the two wheels 2008 by the applied tension forces 2299.

While this invention has been particularly shown and described with references to example embodiments thereof, it will be understood by those skilled in the art that various changes in form and details may be made therein without departing from the scope of the invention encompassed by the appended claims.

The teachings of all patents, published applications and references cited herein are incorporated by reference in their entirety.

REFERENCES

[1] Guo, S., and DiPietro, L. A., Factors affecting wound healing, J Dent Res., 89 (3): 219-229, 2010

[2] Mercandetti, M., and Moinar, J. A., Wound healing and repair, MEDSCAPE REFERENCE, 2011: http://emedicine.medscape.com/Mercandetti.

[3] Witte, M. B., and Barbul, A., General principles of wound healing, Surgical Clinics of North America, 77 (3): 509-528, 1997. Available: http://www.sciencedirect.com/Witte.

[4] Schultz, G. S., Sibbald, R. G., Falanga, V., Ayello, E. A., Dowsett, C., Harding, K., Romanelli, M., Stacey, M. C., Teot, L., and Vanscheidt, W., Wound bed preparation: a systematic approach to wound management, Wound Repair and Regeneration, 11 (2): S1-S28, 2003. Available: http://onlinelibrary.wiley.com/Schultz.

[5] Bradley, M., Cullum, N., and Sheldon, T., The debridement of chronic wounds: a systematic review, Health Technology Assessment, 3 (17): 1-86, 1999. Available: http://www.hta.ac.uk/fullmono/mon3171.pdf.

[6] Gupta, S., Differentiating negative pressure wound therapy devices: an illustrative case series, IN Supplement to WOUNDS, 19 (1): 1-10, 2007.

[7] Sullivan, N., Snyder, D. L., Tipton, K., Uhl, S., Schoelles, K. M., Technology Assessment: Negative pressure wound therapy devices, PREPARED FOR: Agency for Healthcare Research and Quality, 2009. Available: https://www.ecri.org/Documents/Sullivan.

[8] Moore, Z., TECHNOLOGY UPDATE: The important role of debridement in wound bed preparation, Wounds International, 3 (2): 1-4, 2012. Available: http://www-.woundsinternational.com/Moore.

[9] McAleer, J. P., Kaplan, E. M., Persich, G., Axman, W., A prospective randomized study evaluating the time efficiency of the VERSAJET hydrosurgery system and traditional wound debridement. Wound Management, Smith & Nephew, 2006.

[10] Oertel, J, M. R. Gaab, R. Warzok, and J. Pick (2003). Waterjet dissection in the brain: review of the experimental and clinical data with special reference to melingioma surgery. Neurosur Rev 26: 168-174.
[11] Rau, H. G., A. P. Duessel, and S. Wurzbacher (2008). The use of water-jet dissection in open and laparoscopic liver resection. HPB 10: 275-280.
[12] Klein, M. B., S. Hunter, D. M. Heimbach, L. H. Engrav, S. Honari, E. Gallery, D. M Kiriluk, N. S. Gibran (2005). The VERSAJET water dissector: a new tool for tangential excision. J Burn Car Rehabil 26: 483-487.
[13] Granick, M. S., J. Posnett, M. Jacoby, S. Noruthun, P. A. Ganchi, R. O. Datiashvili (2006). Efficacy and cost-effectiveness of a high-powered parallel waterjet for wound debridement. Wound Rep Reg 14: 394-397.
[14] MIST Ultrasound (http://www.misttherapy.com/medical-professionals/the-mist-product/mist-ultrasound/), Misonix SonicOne (http://www.misonix.com/wp-content/uploads/2013/11/SO-OR_2003-12_REV_A_SonicOne_OR_Brochure.pdf); Arobella medical, LLC (http://www.arobella.com/).
[15] Smith & Nephew VERSAJET II Hydrosurgery System, User Guide. Smith & Nephew, Inc., 970 Lake Carillon Drive, St. Petersburg, Fla. 33716; ©2012 Smith & Nephew.
[16] Taberner, Andrew J., Ball, Nathan B., Hogan, N. Catherine, Hunter, Ian W., A portable needle-free jet injector based on a custom high power-density voice-coil actuator, Conference Proceedings IEEE Eng Med Biol Soc., 1: 5001-5004, 2006. Available: http://ieeexplore.ieee.org/Taberner.
[17] Taberner, A. J., Hogan, N. Catherine, and Hunter, I. W., Needle-free jet injection using real-time controlled linear Lorentz-force actuators, Med Engineering & Phys., 34 (9): 1228-1235, 2012. Available: http://www.medengphys.com/Taberner.
[18] Hassinger, S. M., Harding, G., and Wongworawat, M. D., High-pressure pulsatile lavage propagates bacteria into soft tissue, Clinical Orthopaedics and Related Research, 439: 27-31, 2005.
[19] Jones, S. M., Banwell, P. E., and Shakespeare, P. G., Advances in wound healing: topical negative pressure therapy, Postgrad Med J., 81 (956): 353-357, 2005. Available: http://pmj.bmj.com/Jones
[20] Saxena, V., Hwang, C-W, Huang, S., Eichbaum, Q., Ingber, D., and Orgill, D. P., Vacuum-assisted closure: microdeformations of wounds and cell proliferation, Plastic and Reconstructive Surgery, 114 (5): 1086-1096, 2004.
[21] Occupational safety and health guideline for acetic acid. Available: http://www.cdc.gov/niosh/docs/81-123/pdfs/0002-rev.pdf
[22] Hogan, N. Catherine, Hemond, Brian D., Wendell, Dawn M., Taberner, Andrew J., and Hunter, Ian W., Delivery of active collagenase to skin using a Lorentz-force actuated needle-free injector, Conference Proceedings IEEE Eng Med Biol Soc., 1: 5611-5616, 2006. Available: http://ieeexplore.ieee.org/Hogan
[23] Enoch, S., and Harding, K., Wound bed preparation: the science behind the removal of barriers to healing, Wounds 15 (7): 1-27, 2003.

What is claimed is:

1. A debridement apparatus comprising:
a first nozzle delivering a first jet of debridement substance to a region of tissue at a first angle;
a second nozzle positioned a distance away from the first nozzle, the second nozzle delivering a second jet of debridement substance to the region of tissue at a second angle;
a pump or other actuator to drive the first and second jets of debridement substance via a pipe or a hand piece in fluid communication with the first and second nozzles; and
an evacuation chamber supporting a negative pressure, the evacuation chamber positioned between the first and second nozzles, the evacuation chamber including a distal end configured to interface with the region of target tissue, the evacuation chamber stabilizing the region of tissue and removing debrided tissue, contaminants, and exudate through an evacuation lumen coupled to the evacuation chamber, the distal end of the evacuation chamber including a cavity or slot to receive the first and second nozzles;
wherein the first and second jets are adapted to intersect and dissipate into a mist upon intersection, wherein the mist dissipates substantially all of a kinetic energy of the first and second jets, the first and second jets adapted to impact tissue prior to intersection and formation of the mist.

2. The apparatus of claim 1, wherein at least one of the first angle, the second angle, and the distance is adjustable.

3. The apparatus of claim 1,
wherein the first jet and the second jet are driven by the pump or other actuator to control pressure of the debridement substance.

4. The apparatus of claim 3, wherein the pump or other actuator includes at least one Lorentz-force electromagnetic actuator.

5. The apparatus of claim 1, further comprising:
one or more sensors determining one or more of the following: actuator force, positions of the first and second nozzles, orientation of the nozzle, jet pressure, and temperature of the debridement substance or the region of tissue.

6. A method for debriding tissue, the method comprising:
driving a first jet of debridement substance through a first nozzle;
driving a second jet of debridement substance through a second nozzle, the first and second jets intersecting and dissipating into a mist upon intersection, wherein the mist dissipates substantially all of a kinetic energy of the first and second jets;
delivering the first and second jets of debridement substance to a region of tissue, the first and second jets adapted to impact tissue prior to intersection and formation of the mist;
supporting a negative pressure in an evacuation chamber; and
removing the debridement substance after delivery to the region of tissue and additional substances therein through the evacuation chamber;
wherein supporting a negative pressure in an evacuation chamber includes:
disposing the evacuation chamber between the first and second nozzles, the diposing including positioning the first and second nozzles in a cavity or slot in the evacuation chamber;
interfacing with the region of target tissue with a distal end of the evacuation chamber;
stabilizing the region of tissue; and
removing any combination of tissue, contaminants, and exudate through an evacuation lumen connected to the evacuation chamber.

7. The method of claim 6, further comprising:
controlling a pressure of the debridement substance with a controllable pressure source, the controllable pressure source driving the first jet of debridement substance through the first nozzle and the second jet of debridement substance through the second nozzle.

8. The method of claim 6, further including tensioning the region of tissue during the delivering the first and second jets of debridement substance to the region of tissue.

9. A debridement apparatus comprising:
a first nozzle delivering a first jet of debridement substance to a region of tissue at a first angle;
a second nozzle positioned a distance away from the first nozzle, the second nozzle delivering a second jet of debridement substance to the region of tissue at a second angle; and
an evacuation chamber supporting a negative pressure, the evacuation chamber positioned between the first and second nozzles, the evacuation chamber including a distal end configured to interface with the region of target tissue, the evacuation chamber stabilizing the region of tissue and removing debrided tissue, contaminants, and exudate through an evacuation lumen coupled to the evacuation chamber, the distal end of the evacuation chamber including a cavity or slot to receive the first and second nozzles;
wherein the first and second jets are adapted to intersect and dissipate into a mist upon intersection, wherein the mist dissipates substantially all of a kinetic energy of the first and second jets.

10. A method for debriding tissue, the method comprising:
driving a first jet of debridement substance through a first nozzle;
driving a second jet of debridement substance through a second nozzle, the first and second jets intersecting and dissipating into a mist upon intersection, wherein the mist dissipates substantially all of a kinetic energy of the first and second jets;
delivering the first and second jets of debridement substance to a region of tissue;
supporting a negative pressure in an evacuation chamber; and
removing the debridement substance after delivery to the region of tissue and additional substances therein through the evacuation chamber;
wherein supporting a negative pressure in an evacuation chamber includes:
positioning the first and second nozzles in a cavity or slot in the evacuation chamber disposed between the first and second nozzles;
interfacing with the region of target tissue with a distal end of the evacuation chamber;
stabilizing the region of tissue; and
removing any combination of tissue, contaminants, and exudate through an evacuation lumen connected to the evacuation chamber.

* * * * *